United States Patent
Parsons et al.

(10) Patent No.: US 6,703,216 B2
(45) Date of Patent: Mar. 9, 2004

(54) METHODS, COMPOSITIONS AND APPARATUSES FOR DETECTION OF GAMMA-HYDROXYBUTYRIC ACID (GHB)

(75) Inventors: Stanley M. Parsons, Santa Barbara, CA (US); David O. Harris, Santa Barbara, CA (US); Dawn T. Bravo, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/098,811

(22) Filed: Mar. 14, 2002

(65) Prior Publication Data

US 2003/0175846 A1 Sep. 18, 2003

(51) Int. Cl.[7] .............................. C12Q 1/26; C12Q 1/32; C12Q 1/44; C12Q 1/37; G01N 33/53

(52) U.S. Cl. .............................. 435/25; 435/26; 435/19; 435/23; 435/24; 435/968; 435/975; 435/283.1; 435/970; 435/287.1; 435/69.1; 435/91.4; 435/320.1

(58) Field of Search .............................. 435/25, 26, 19, 435/23, 24, 968, 975, 283.1, 970, 287.1, 69.1, 91.4, 320.1

(56) References Cited

U.S. PATENT DOCUMENTS

| | | | |
|---|---|---|---|
| 3,715,192 A | 2/1973 | Wenz et al. | 435/25 |
| 3,915,639 A | 10/1975 | Friedenberg | 435/25 |
| 3,965,750 A | 6/1976 | Johnson | 435/25 |
| 3,994,170 A | 11/1976 | Czarnecki | 435/25 |
| 4,092,115 A | 5/1978 | Rupe et al. | 435/25 |

(List continued on next page.)

FOREIGN PATENT DOCUMENTS

| | | |
|---|---|---|
| EP | A 0 125 118 B1 | 11/1984 |
| EP | A 0 143 574 | 6/1985 |

(List continued on next page.)

OTHER PUBLICATIONS

Ishigro et al, Brain Dev. V.23(2), p. 128–130, Abstract Only, (2001).*

(List continued on next page.)

Primary Examiner—Louise N. Leary
(74) Attorney, Agent, or Firm—Bingham McCutchen LLP; David W. Maher

(57) ABSTRACT

Methods, compositions and articles of manufacture for assaying a sample for a GHB source are provided. A sample suspected of containing a GHB source is contacted with a first oxidoreductase selective for GHB and an oxidized cofactor. In the presence of GHB in the sample, the first oxidoreductase oxidizes GHB to succinic semialdehyde and reduces the cofactor. The reduced cofactor thus produced can be detected directly, or a hydride abstractor can be used that abstracts a hydride from the reduced cofactor and produces a detectable change. The hydride abstractor can be a second oxidoreductase that oxidizes the reduced cofactor and produces a detectable change in a chromogen or dye. Preferably a visual change is produced, allowing performance of the assay outside of a laboratory setting. Fusion proteins comprising the first oxidoreductase, polynucleotides encoding such proteins, host cells expressing such proteins, and vectors comprising such polynucleotides are also provided. Stabilized formulations of the first oxidoreductase are also provided. Test supports, devices, and compositions and kits comprising reagents for performing such methods are also provided. Techniques for performing the assay in the presence of ethanol and in the presence of GHB precursors in the sample are also provided.

73 Claims, 10 Drawing Sheets

(6 of 10 Drawing Sheet(s) Filed in Color)

U.S. PATENT DOCUMENTS

| | | | |
|---|---|---|---|
| 4,157,664 A | 6/1979 | Robinson | 435/25 |
| 4,254,222 A | 3/1981 | Owen | 435/26 |
| 4,313,734 A | 2/1982 | Leuvering | 23/999.999 |
| 4,348,205 A | 9/1982 | Lipton et al. | 23/999.999 |
| 4,351,899 A | 9/1982 | Owen | 435/26 |
| 4,366,241 A | 12/1982 | Tom et al. | 435/7 |
| 4,394,449 A | 7/1983 | Modrovich | 435/188 |
| 4,625,574 A | 12/1986 | Robbins | 73/864.63 |
| 4,632,901 A | 12/1986 | Valkirs et al. | 435/5 |
| 4,743,559 A | 5/1988 | Koéver et al. | 436/175 |
| 4,770,853 A | 9/1988 | Bernstein | 422/58 |
| 4,786,589 A | 11/1988 | Rounds | 435/5 |
| 4,816,567 A | 3/1989 | Cabilly et al. | 530/387 |
| 4,892,817 A | 1/1990 | Pawlak | 435/21 |
| 4,910,141 A | 3/1990 | Wong et al. | 435/172.3 |
| 5,037,738 A | 8/1991 | Lamos et al. | 435/12 |
| 5,190,863 A | 3/1993 | Magers | 435/25 |
| 5,326,697 A | 7/1994 | Magers | 435/25 |
| 5,380,937 A | 1/1995 | Koehler et al. | 562/572 |
| 5,426,040 A | 6/1995 | Cheney et al. | 435/172.2 |
| 5,484,708 A | 1/1996 | Hoenes et al. | 435/14 |
| 5,504,013 A | 4/1996 | Senior | 436/165 |
| 5,510,245 A | 4/1996 | Magers | 435/26 |
| 5,527,509 A | 6/1996 | Gibson et al. | 422/56 |
| 5,583,006 A | 12/1996 | Storhoff et al. | 435/14 |
| 5,583,044 A | 12/1996 | Ruksenas et al. | 435/287 |
| 5,589,349 A | 12/1996 | Shinzaki et al. | 435/26 |
| 5,611,995 A | 3/1997 | de Zoeten et al. | 422/58 |
| 5,618,686 A | 4/1997 | Kojima et al. | 435/26 |
| 5,624,813 A | 4/1997 | Mahant | 435/28 |
| 5,633,143 A | 5/1997 | Ueda et al. | 435/26 |
| 5,637,473 A | 6/1997 | Clemmons | 435/7.91 |
| 5,652,043 A | 7/1997 | Nitzan | 428/209 |
| 5,656,448 A | 8/1997 | Kang et al. | 435/7.94 |
| 5,710,011 A | 1/1998 | Forrow et al. | 435/25 |
| 5,728,076 A | 3/1998 | Loos et al. | 604/232 |
| 5,753,708 A | 5/1998 | Koehler et al. | 514/629 |
| 5,766,874 A | 6/1998 | Miyada et al. | 435/26 |
| 5,770,460 A | 6/1998 | Pawlak et al. | 435/510 |
| 5,783,382 A | 7/1998 | Aoyama et al. | 435/4 |
| 5,786,220 A | 7/1998 | Pronovost et al. | 436/518 |
| 5,801,006 A | 9/1998 | Kaufman | 435/15 |
| 5,804,402 A | 9/1998 | De Giorgio et al. | 435/26 |
| 5,804,403 A | 9/1998 | Dorn et al. | 435/26 |
| 5,811,204 A | 9/1998 | Nitzan | 429/127 |
| 5,840,331 A | 11/1998 | Van Cauter et al. | 424/464 |
| 5,861,269 A | 1/1999 | Visor et al. | 435/26 |
| 5,871,949 A | 2/1999 | Ebinuma et al. | 435/26 |
| 5,897,522 A | 4/1999 | Nitzan | 604/20 |
| 5,902,731 A | 5/1999 | Ouyang et al. | 435/26 |
| 5,912,139 A | 6/1999 | Iwata et al. | 435/26 |
| 5,990,162 A | 11/1999 | Scharf | 514/533 |
| 6,121,010 A | 9/2000 | Vallee et al. | 435/26 |
| 6,153,147 A | 11/2000 | Craig | 422/59 |
| 6,156,431 A | 12/2000 | Kitchen et al. | 428/405 |
| 6,187,269 B1 | 2/2001 | Lancesseur et al. | 422/61 |
| 6,190,918 B1 | 2/2001 | Chu et al. | 436/63 |
| 6,235,241 B1 | 5/2001 | Catt et al. | 422/56 |
| 6,329,209 B1 | 12/2001 | Wagner et al. | 435/518 |

FOREIGN PATENT DOCUMENTS

| | | |
|---|---|---|
| EP | A 0 282 192 | 9/1988 |
| EP | A 0 299 359 | 1/1989 |
| EP | A 0 299 428 B1 | 1/1989 |
| GB | 2276169 A | 9/1994 |
| WO | WO 88/08534 | 11/1988 |
| WO | WO 00/04382 | 1/2000 |
| WO | WO 00/04389 | 1/2000 |
| WO | WO 00/04390 | 1/2000 |
| WO | WO 01/51912 A1 | 7/2001 |
| WO | WO 01/62887 A1 | 8/2001 |
| WO | WO 01/63241 | 8/2001 |
| WO | WO 01/72458 A1 | 10/2001 |

OTHER PUBLICATIONS

Hoffman et al, Adv. Exp. Med. Biol, V. 132, p. 749–759, Abstract Only, (1980).*

Gibson et al, Clin. Chim Acta, V. 133(1), p. 33–42, Abstract Only, (Sep. 1983).*

Andriamampandry, C., et al., "Cloning of a rat brain succinic semialdehyde reductase involved in the synthesis of the neuromodulator γ–hydroxybutyrate," *Biochem. J.*, 1998, 334–43–50.

Atherton et al., Solid Phase Peptide Synthesis: A Practical Approach, IRL Press, 1989, 1–12.

J.F. Biellman and M.J. Jung, "Preparation and Properties of 3–CYANO Pyridine Ad$^{30}$, A New Analogue of NAD$^{+}$", *FEBS Lett.*, 1970, 7(2):199–200.

Cho, S.W., et al., "Kinetics and mechanism of an NADPH–dependent succinic semialdehyde reductase from bovine brain", *Eur. J. Biochem.*, 1993, 211:757–762.

Cho, S.W., et al., "Interaction of an NADPH–dependent succinic semialdehyde reductase by 0–phthaladehyde," *FEBS Letters*, 1996, 382:179–182.

Choi, E.Y., et al., "Production and characterization of monoclonal antibodies to bovine brain succinic semialdehyde reductase," *J. Neurochem.*, 1995, 64:371–377.

Chou, P.Y. and Fasman, G.D., "Prediction of the Secondary Structure of Proteins from Their Amino Acid Sequence," *Advances in Enzymology*, 1978, 47:45–148.

Cole et al., "The EBV–Hybridoma Technique and its Application to Human Lung Cancer," *Monoclonal Antibodies and Cancer Therapy*, Alan R. Liss, 1985, p. 77.

Cromlish, J.A., "Identification of Pig Brain Aldehyde Reductase with the High–$K_m$ Aldehyde Reductase, the Low–$K_m$ Aldehyde Reductase and Aldose Reductase, Carbonyl Reductase, and Succinic Semialdehyde Reductase," *J. Neurochem.*, 1985, 44:1485–1493.

Cumber et al., "Comparative Stabilities In Vitro and In Vivo of a Recombinant Mouse Antibody FvCys Fragment and A bisFvCys Conjugate," *J. Immunology*, 1992, 149B:120–126.

Doolittle, R.F., "Reconstructing history with amino acid sequences," *Protein Sci.*, 1992, 1:191–200.

Doolittle, R.F., et al., "Relationships of Human Protein Sequences to Those of Other Organisms," *Cold Spring Harbor Symposia*, 1986, 51:447–455.

Ehrlich, P.H., et al., "Isolation of an Active Heavy–Chain Variable Domain from a Homogeneous Rabbit Antibody by Cathespin B Digestion of the Aminoethylated Heavy Chain," *Biochem.*, 1980, 19:4091–4096.

E.M. Ellis and J.D. Hayes, "Substrate specificity of an aflatoxin–metabolizing aldehyde reductase", *Biochem. J.*, 1995, 312:535–541.

Everse, J., et al., "The Pyridine Nucleotide Coenzymes", *Academic Press*, New York, 1982, pp. 92–133.

Ferrera, S.D., et al., "Therapeutic gamma–hydroxybutyric acid monitoring in plasma and urine by gas chromatography–mass spectrometry," *Journal of Pharmacology and Biomedical Analysis*, 1993, 11:6, 483–487.

Galloway, G.P., et al., "Abuse and therapeutic potential of gamma–hydroxybutyric acid," *Alcohol*, 2000, 20:263–269.

Gibson, K.M., et al., "Stable Isotope Dilution Analysis of 4–Hydroxybutyric Acid: An Accurate Method for Quantification in Physiological Fluids and the Prenatal Diagnosis of 4–Hydroxybutyric Aciduria," *Biomed. and Environ. Mass Spectrometry*, 1990, 19:89–93.

Henne, A., et al., "Construction of Environmental DNA Libraries in *Escherichia coli* and Screening for the Presence of Genes Conferring Utilization of 4–Hydroxybutyrate," *Appl. Environ. Microbiol.*, 1999, 65:3901–3907.

Herrscher, R.F., et al., "The immunoglobulin heavy–chain matrix–associating regions are bound by Bright: a B cell–specific trans–activator that describes a new DNA–binding protein family," *Genes Dev.*, 1995, 9:3067–3082.

Hitzeman, R.A., et al., "Isolation and Characterization of the Yeast 3–Phosphoglycerokinase Gene (PGK) by an Immunological Screening Technique," *J. Biol. Chem.*, 1980, 255:12073–12080

Hong, J.W., et al., "Modulation of the catalytic activity of brain succinic semialdehyde reductase by reaction with pyridoxal 5'–phosphate," *Eur. J. Biochem.*, 1997, 247:274–279.

Hunger, H., et al., "Nucleic Acid Fixation to Cyanuric Chloride–Activated Paper," *Biochim. Biophys. Acta*, 1981, 653:344–349.

Huston, J.S., et al., "Protein engineering of antibody binding sites: Recovery of specific activity in and anti–digoxin single–chain Fv analogue produced in *Escherichia coli*," *Proc. Natl. Acad. Sci. USA.*, 1988, 85:5879–5883.

Inbar, D., et al., "Localization of Antibody–Combining Sites within the Variable Portions of Heavy and Light Chains," *Proc. Natl. Acad. Sci. USA.*, 1972, 69:2659–2662.

Jendrossek, D., et al., "Characterization of Alcohol Dehydrogenase Genes of Derepressible Wild–Type *Alcaligenes eutropus* H16 and Constitutive Mutants," Bacteriol, 1990, 172 ():4844–4861.

Kaplan N.O., et al., "Chemistry and Properties of the 3–Acetylpyridine Analogue of Diphosphopyridine Nucleotide," *J. Biol. Chem.*, 1956, 221:823–832.

Kaplan, N.O., et al., "Reaction of Pyridine Nucleotide Analogues with Dehydrogenases," *J. Biol. Chem.*, 1956, 221:833–844.

Kaufman, R.J., et al., "Translational efficiency of polycistronic mRNAs and their utilization to express heterologous genes in mammalian cells," *EMBO J.*, 1987, 6:187–193.

E.E. Kaufman and T. Nelson, "Kinetics of Coupled γ–hydroxybutyrate oxidation and D–Glucuronate Reduction by an $NADP^+$–dependent Oxidoreductase," *J. Biol. Chem.*, 1981, 256 (13):6890–6894.

Kaufman et al., "Regulation and Properties of an $NADP^+$ Oxidoreductase Which Functions as a γ–Hydroxybutyrate Dehydrogenase," *J. Neurochem.*, 1983, 40:1639–1646.

E.E. Kaufman and T. Nelson, "An Overview of γ–Hydroxybutyrate Catabolism: The Role of the Cytosolic $NADP^+$ – Dependent Oxidoreductase EC 1.1.1.19 and of a Mitochondrial Hydroxyacid–Oxoacid Transhydrogenase in the Initial, Rate–Limiting Step in This Pathway," *Neurochem. Res.*, 1991, 16:965–974.

Kemmel, V., et al., "Neurochemical and Electrophysiological Evidence for the Existence of a Functional γ–Hydroxybutyrate System in NCB–20 Neurons," *Neurosci.*, 1998, 86:989–1000.

Kopetzki, E., et al., "Control of formation of active soluble or inactive insoluble baker's yeast α–glucosidase Pl in *Escherichia coli* by induction and growth conditions," *Mol Gen Genet*, 1989, 216:149–255.

Kuhn, M., et al., "Cloning of the *Alcaligenes eutrophus* Alcohol Dehydrogenase Gene," *J. Bacteriol*, 1988, 170:685–692.

J. Kyte and R.F. Doolittle, "A Simple Method for Displaying the Hydropathic Character of a Protein," *J. Mol. Biol.*, 1982, 157:105–132.

Leonard, S.A., "Gamma–hydroxybutyrate Effects and Regulation," *OLR Research Report*, Aug. 17, 1999, #99–R–0825, pp. 1–4.

J. Letteri and H. Fung, "Dose–Dependent Pharmacokinetics and Hypnotic Effects of Sodium γ–Hydrobutyrate in the Rat," *Journal of Pharmacology and Experimental Therapeutics*, 1979, 208 (1):7–11.

McCusker, R.R., et al., "Analysis of Gamma–Hydroxybutyrate (GHB) in Urine by Gas Chromatography–Mass Spectrometry," *Journal of Analytical Toxicology*, Sep. 1999, 23(5):301–5.

M.Z. Mesmer and R.D. Satzger, "Determination of Gamma–Hydroxybutyrate (GHB), and Gamma–Butyrolactone (GBL) by HPLC/UV–VIS Spectrophotometry and HPLC/Thermospray Mass Spectrometry," *J. of Forensic Sci.*, May 1998, 43(3):489–492.

T. Nelson and E.E. Kaufman, "Developmental Time Courses in the Brain and Kidney of Two enzymes that Oxidize γ–Hydroxybutyrate," *Dev. Neurosci.*, 1994, 16:352–358.

Nilsson, B., et al., "Immobilization and purification of enzymes with staphylococcal protein A gene fusion vectors," *EMBO J.*, 1985, 4(4):1075–1080.

Oppenheimer, N.J., "Pyridine Nucleotide Coenzymes—Chemical Stability and Reactivity of Pyridine Nucleotide Coenzymes," *Coenzymes and Cofactors*, John Wiley, New York, 1987, 3:324–365.

P. Pack and A. Plückthun, et al., "Miniantibodies: Use of Amphipathic Helices To Produce Functional, Flexibly Linked Dimeric Fv Fragments with High Avidity in *Escherichia coli*," *Biochem*, 1992, 31(6):1579–1584.

J. Renart and I.V. Sandoval, "Western Bolts," *Methods in Enzymol.*, 1984, 104:455–460.

Renart, J., et al., "Transfer of proteins from gels to diazobenzyloxymethyl–paper and detection with antisera: A method for studying antibody specificity and antigen structure," *Proc. Natl. Acad. Sci.*, 1979, 76:3116.

Reichmann, L. et al., "Reshaping human antibodies for therapy," *Nature*, 1988, 332:323–327.

Rej, R., "Review: The Role of Coenzymes in Clinical Enzymology," *Annals of Clinical and Laboratory Science*, 1977, 7(6):455–468.

Rodrigues, M.F.A., et al., "Polyhydroxyalkanoate accumulation in *Burkholderia* sp.: a molecular approach to elucidate the genes involved in the formation of two homopolymers consisting of short–chain–length 3–hydroxyalkanoic acids," *Appl. Microbiol. Biotechnol.*, 2000, 53:453–460.

Schaller, M., et al., "Cloning and expression of succinic semialdehyde reductase from human brain," *Eur. J. Biochem.*, 1999, 265:1056–1060.

Schmitt et al., "Justice, with tears . . . ,", *Detroit Free Press*, Mar. 15, 2000, pp. 1–3.

Scott Company, Products for GHB Indentification: Drug Test, GHB Test, www.scottcompany.com/public_html/products,GHB.html., Mar. 17, 2003 (3 pgs.).

Seed et al., "Diazotizable arytamine cellulose papers for the coupling and hybrization of nucleic acids," *Nucleic Acids Res.*, 1982, 10:1799–1810.

Segel, I.H., *Enzyme Kinetics*, J. Wiley & Sons, New York, NY, 1975, pp. 18–21.

Serva Tetrazolium Salts—Data Sheet, "Tetrazolium Salts—highly sensitize colour indicators of enzymatic redox reactions," www.serva.de/products/latest/tetrazolium.shtml, Oct. 18, 2001 (5 pgs.).

B. Söhling and G. Gottschalk, "Molecular Analysis of the Anaerobic Succinate Degradation Pathway in *Clostridium kluyveri,*" *J. Bacteriol*, 1996, 178:871–880.

Substance Abuse and Mental Health Services Administration, "Club Drug", *The Dawn Report*, Dec. 2000, pp. 1–10.

Valentin, H.E., et al., "Metabolic pathway for biosynthesis of poly(3–hydroxybutyrate–co–4–hydrobutyrate) from 4–hydroxybutyrate by *Alcaligenes eutrophus,*" *Eur. J. Biochem.*, 1995, 227:43–60.

H.E. Valentin and D. Dennis, "Production of poly(3–hydroxybutyrate–co–4–hydroxybutyrate) in recombinant *Escherichia coli* grown on glucose," *J. Biotech.*, 1997, 58:33–38.

Valentin, H.E., et al., "Poly(3–hydroxybutyrate–co–4–hydroxybutyrate) formation from γ–aminobutyrate and glutamate," *Biotechnol. Bioengin.*, 2000, 67:291–299.

Verhoeyan, M., et al., "Reshaping Human Antibodies: Grafting and Antilysozyme Activity," *Science*, 1988, 239:1534–1536.

G. Winter and C. Milstein, "Man–made antibodies," *Nature*, 1991, 349:293–299.

R.A. Wolff and W.R. Kenealy, "Purification and characterization of the Oxygen–Sensitive 4–Hydroxybutanoate Dehydrogenase from *Clostridium kluyveri,*" *Prot. Express. Purif.*, 1995, 6:206–212.

United Chemical, Clean Screen GHB: Clean Screen ®, www.unitedchem.com/1024x768/ghb.htm, Jan. 4, 2002 (3 pgs.).

Yoshie, N., et al., "Biosynthesis and n.m.r studies of deuterated poly(3–hydroxybutyrate) produced by *Alcaligenes eutrophus*, H16." *Int. J. Biol. Macromol*, 1992, 14:81–86.

Zatman, L.J., et al., "Effect of Isonicotinic Acid Hydrazide on Diphosphopyridine Nucleotideases," *J. Biol. Chem.*, 1954, 209:453–466.

Zatman, L.J., et al., "The isolation and Properties of the isonicotinic Acid Hydrazide Analogue of Diphospyridine Nucleotide," *J. Biol. Chem.*, 1954, 209:467–484.

Mash, Deborah C., Abstract for Rapid Screening Method: Gamma–hydroxybutyrate Detection, Grant No.: 5R21DA014912.02, Era Commons, Computer Retrieval of Information on Scientific Projects (Crisp), publication date: Nov. 19, 2001, https://www–commons.cit.nih.gov/crisp/.

\* cited by examiner

```
gene 5120..6268
gene="gbd"
CDS  5120..6268
gene="gbd"
EC_number="1.1.1.61"
codon_start=1
_table=11
product="NAD-dependent 4-hydroxybutyrate dehydrogenase"
protein_id="AAC41425.1"
db_xref="GI:695279"
translation="MAFIYYLTHIHLDFGAVSLLKSECERIGIRRPLLVTDKGVVAAG
VAQRAIDAMQGLQVAVFDETPSNPTEAMVRKAAAQYREAGCDGLVAVGGGSSIDLAKG
IAILATHEGELTTYATIEGGSARITDKAAPLIAVPTTSGTGSEVARGAIIILDDGRKL
GFHSWHLLPKSAVCDPELTLGLPAGLTAATGMDAIAHCIETFLAPAFNPPADGIALDG
LERGWGHIERATRDGQDRDARLNMMSASMQGAMAFQKGLGCVHSLSHPLGGLKIDGRT
GLHHGTLNAVVMPAVLRFNADAPTVVRDDRYARLRRAMHLPDGADIAQAVHDMTVRLG
LPTGLRQMGVTEDMFDKVIAGALVDHCHKTNPKEASAADYRRMLEQSM"
```

```
5120                       a tggcgtttat ctactatctg acccacatcc acctggattt
5161 cggcgcggta agcctgctca agtccgaatg cgagcgcatc ggcatccgcc gcccgttgct
5221 ggtgaccgac aagggcgtgg tcgccgcggg agtggcgcag cgtgccatcg atgcaatgca
5281 gggcctgcag gttgcggtat tcgatgaaac cccgtcgaac ccgaccgagg ccatggtgcg
5341 caaggccgcc gcacaatacc gcgaggccgg ctgcgacggg ctggtggcag tgggcggcgg
5401 ctcgtcgatc gacctcgcca agggcatcgc catcctggcc acgcatgagg gcgagctgac
5461 cacctatgcc accatcgaag cggcagcgc caggatcacc gacaaggcgg cgccgctgat
5521 cgcggtgccc accacctcgg gcaccggcag cgaggtggcg cgcggcgcca tcatcatcct
5581 ggacgacggc cgcaagctgg gcttccattc ctggcatttg ctgcccaagt ccgccgtctg
5641 cgaccggaa ctgacgctgg gctgccggc cgggctgacc gcggccaccg gcatggatgc
5701 gatcgcgcac tgcatcgaga ccttcctggc ccccgccttc aacccgcccg cggacggcat
5761 tgcgctggac gggctggagc gcggctgggg ccatatcgaa cgcgccaccc gcgacggtca
5821 ggaccgcgac gcacgcctga acatgatgag cgcgtcgatg cagggcgcaa tggcgttcca
5881 gaaggggctg ggctgcgtgc attcgctgtc gcacccgctg ggcgggctga agatcgacgg
5941 ccgcaccggc ctgcaccacg gcacgctcaa cgcggtggtg atgccggcgg tgctgcgctt
6001 caacgccgat gcgcccacgg tggtgcgcga cgaccgctac gcacgcctgc gccgcgccat
6061 gcacctgccc gacggcgccg atatcgcgca ggccgtgcac gacatgaccg tgcgcctggg
6121 cctgcccacc gggctgcgtc agatgggtgt caccgaggac atgttcgaca aggtgattgc
6181 cggtgcgctg gtcgaccatt gccacaagac caacccgaaa gaagccagcg ccgcggatta
6241 tcggcgtatg cttgagcagt ccatgtag
```

Figure 2

ID
METHODS, COMPOSITIONS AND APPARATUSES FOR DETECTION OF GAMMA-HYDROXYBUTYRIC ACID (GHB)

TECHNICAL FIELD

This invention relates to methods, compositions and articles for assaying a sample for an analyte.

BACKGROUND OF THE INVENTION

A colorless, odorless, tasteless chemical has become one of the most dangerous illicit drugs of abuse today. The drug is a central nervous system (CNS) depressant at low doses, and has the curious effects of reducing anxiety and producing euphoria and relaxation, sedating the recipient. The drug also is naturally present in the body and has a short half-life, making detection of ingested drug difficult (S. D. Ferrara et al., Journal of Pharmacology and Biomedical Analysis, 11:6, 483–487, 1993).

Because of these properties, the drug has been abused through surreptitious administration to unsuspecting users in a variety of settings, including college parties and bars. The drug has thus become known as one of the "date rape" drugs, used to disable women who have unknowingly ingested the drug in a product they otherwise intended to consume.

The drug has risks beyond unintended disinhibition, however. The drug can cause unconsciousness, respiratory depression, bradycardia, nausea, vomiting, seizures and coma, and has been linked to over 60 deaths. The severity of symptoms and the duration of action are dose dependent and can be affected by the presence of other CNS depressants. Recently, male perpetrators who mixed the drug in the drinks of unsuspecting females were convicted of involuntary manslaughter in the death of one 15-year-old recipient who died as a result ("Justice, with tears," Schmitt et al., Detroit Free Press, Mar. 15, 2000).

The dangers of such results are an inherent property of the drug, and one that makes its illicit use particularly dangerous. The drug has a very steep dose-response curve. A 1-gram dose for a 150-pound person provides a low degree of effect, causing a sense of euphoria and loss of inhibitions (Leonard, 1999; Galloway, 2000). However, a 2.5-gram dose to the same individual can lead to coma (ibid.). Higher doses can result in death.

Despite the rapid rise in the degree of abuse of this drug, the available methods for assaying GHB are either insensitive or cumbersome, difficult, time-consuming, expensive and equipment-intensive (J. Letteri and H. Fung, Journal of Pharmacology and Experimental Therapeutics, 208, 7–11, 1979). Given the short half-life of the compound and the public settings in which it is used and abused, it is currently difficult at best to assay for its presence, and cannot be done routinely and practically in public venues where it is most often abused, such as bars. The time-consuming nature or insensitivity of the available assays also impedes rapid treatment of overdose victims, particularly when they are unconscious or otherwise unaware of having ingested anything, because proper therapy is dictated by knowledge of the kind of overdose being treated.

The drug is gamma-hydroxybutyric acid (GHB). GHB was widely used for a number of years as a freely available, over the counter supplement. Bodybuilders used GHB for its reported effects of inducing the release of growth hormone from the anterior pituitary. GHB has a number of potentially useful therapeutic properties, and has been used as an anesthetic and in the treatment of insomnia, narcolepsy, drug addiction, and withdrawal symptoms. GHB has been suggested to be a natural neurotransmitter; receptors for it have been detected in the brain, and mechanisms for the synthesis, release and uptake of GHB in the brain have been characterized. GHB is also chemically related to the brain's major inhibitory neurotransmitter, gamma-aminobutyric acid (GABA).

Although GHB was previously readily available, abuse has led to its sale and use being highly restricted. Hospital emergency room visits resulting from the use of GHB increased from 55 in 1994 to 2,973 in 1999 (The DAWN Report, December 2000, Substance Abuse and Mental Health Services Administration). The dangers from the drug were thought to be so high that a federal law was enacted identifying GHB as an imminent hazard to public safety and directing the Attorney General to classify GHB as a "Schedule 1" drug under the Controlled Substances Act, increasing the penalties for its illicit use (H.R. 2130/S. 1561, the Hillory J. Farias and Samantha Reid Date-Rape Drug Prohibition Act of 2000'). Unfortunately, metabolic precursors to GHB such as gamma-butyrolactone (GBL) and 1,4-butanediol remain readily available, and are subject to the same forms of abuse.

Despite the serious recognized problems presented by GHB use, until very recently there has been no field test available that allows the detection of GHB under real-world conditions that can address the current methods of abuse. Known methods of GHB detection are laborious, requiring multiple steps, expensive instrumentation, and trained technicians to perform them, or they are too insensitive to detect GHB at concentrations commonly abused. While existing methods could be used to detect GHB in forensic samples after a victim or suspect has already been identified, they cannot practically be applied routinely on multiple samples in the field prior to ingestion. A recently developed chemical field method is very insensitive and does not reliably detect the concentration of GHB typically present in adulterated drinks.

For example, gas chromatography-mass spectrometry methods for detecting GHB have been described (McCusker et al., Journal of Analytical Toxicology Sep. 23, 1999(5): 301–5; Gibson et al., Biomed. and Environ. Mass Spectrometry, 19, 89–93, 1990). Gas chromatographic methods may not detect GHB directly, as GHB can be converted to the lactone form at injector temperatures. Additionally, detection methods can involve acidification steps coupled with extraction and/or gas chromatography; such acidification converts any GHB present to GBL. This is problematic, as the lactone form is not illegal per se. A method for detecting GHB that avoids detection of gamma-butyrolactone was discussed in U.S. Pat. No. 6,156,431.

HPLC methods of detecting GHB were described by M. Z. Mesmer and R. D. Satzger (J. of Forensic Sci., 43(3), 489–492, May, 1998). Both methods involve reverse phase HPLC, which is coupled with UV detection at 215 nm in the first method, and with thermospray mass spectrometry in the second. These methods can resolve GHB and GBL via HPLC. Both methods require expensive laboratory equipment and a trained laboratory technician to operate them. Furthermore, the methods may lack the sensitivity needed to detect the compound(s) in dilute samples such as adulterated drinks or metabolic fluids. The first method additionally requires a sample lacking UV absorbing substances.

The Scott Company (133 Red Oak Lane, Flower Mound, Tex. 75128; 972-539-0229) recently introduced a chemical color test for GHB. A Q-tip® is soaked in the solution to be tested and placed in a small vial containing a yellow solution. A change in color from yellow to brown indicates the presence of GHB. Analysis of different GHB concentrations using the Scott kit demonstrated that 300 mM GHB gives a weak positive test. This is a very high concentration of GHB that in a 4-ounce drink could cause death. GHB commonly is abused at lower concentrations that yield negative tests with the Scott kit. Also, the Scott test does not detect precursors to GHB.

There is a need in the art for new methods of analyzing GHB in a sample, and for devices, compositions and articles of manufacture useful in such methods.

SUMMARY OF THE INVENTION

Methods, compositions and articles for enzymatically assaying a sample for a GHB source are provided. The methods advantageously employ a first oxidoreductase that can oxidize 4-hydroxybutyric acid. Conversion of this acid to succinic semialdehyde through the enzymatic activity of the oxidoreductase is coupled to the reduction of a cofactor for the first oxidoreductase. The reduced form of this cofactor can be assayed directly, for example spectrophotometrically to detect changes in absorbance of the cofactor following reduction. Or additional enzymatic methods may be employed which utilize the reduced cofactor to produce a detectable signal.

Preferably, a hydride abstractor is used which abstracts a hydride from the reduced cofactor and produces a detectable change. The detectable change can occur in the hydride abstractor or in another molecule. Preferably, a second oxidoreductase is employed as the hydride abstractor, and the detectable change occurs in a chromogen or dye that is reduced by the second oxidoreductase in concert with oxidation of the reduced cofactor. Where the method is performed as a field test outside a laboratory setting, the detectable change is preferably a visually detectable change in the chromogen or dye which permits assay results to be visually determined.

The methods can be used in solution or can take place on or within a support, for example on a test strip. Positive controls containing known GHB sources may also be employed. When performed on a support such as a test strip, the positive control(s) may be deposited in a detectable pattern to allow for easier detection of a positive result. Reagents for performing the assay on the test sample can also be deposited on the support, providing a defined area in which a positive result is determined. Different chromogens and/or dyes can be used which produce different detectable changes, for example different color changes, to allow for use of the assay on a samples of various colors, and may be fixed on different regions of the support.

The methods can be employed on a single sample or on multiple samples, for example in a multiwell or other array format. The methods can be used to detect a GHB source in a sample, and can also be used to quantitate the amount of a GHB source present in the sample.

The methods can incorporate additional techniques to detect precursor sources of GHB. For example, an esterase may be included in the assay to allow detection of esterified forms of GHB, including the internal ester gamma-butyrolactone. Comparison of assay results in the presence and absence of such an esterase allows the method to distinguish between GHB and esterified forms in the sample. The methods can also employ steps for altering or removing ethanol from the sample to prevent a false positive result from occurring where the first oxidoreductase can use ethanol as an alternative substrate.

Compositions comprising reagents useful for performing the assay are also provided. Kits comprising reagents useful for performing the methods of the invention are also provided. The methods, compositions and articles can be used as alternatives to other methods of assaying samples for GHB.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 2 shows the *Ralstonia eutropha* 4-hydroxybutyrate dehydrogenase amino acid (SEQ ID NO: 1) and gene (SEQ ID NO: 2) sequences.

DETAILED DESCRIPTION OF THE INVENTION

Figure 1:
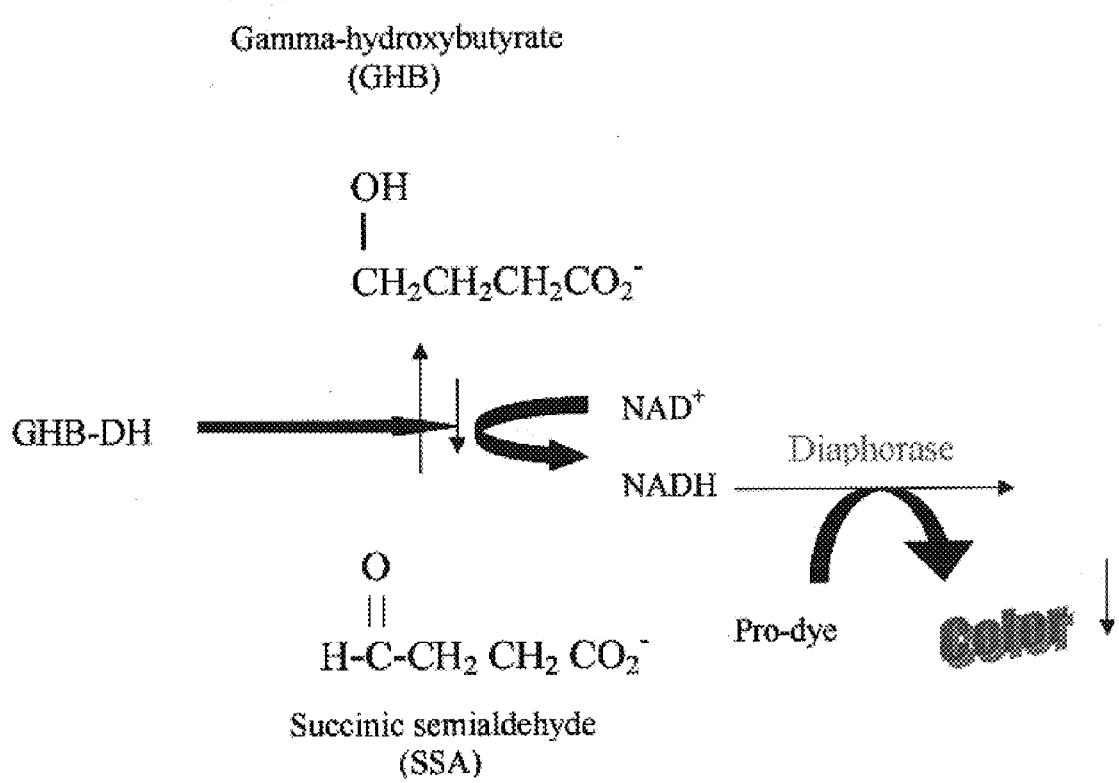
FIG. 1 shows the reaction scheme for a GHB assay using 4-hydroxybutyrate dehydrogenase (also referred to as GHB dehydrogenase or GHB-DH) from the bacterium *Ralstonia eutropha*.

Methods, compositions and articles for analyzing a sample for a GHB source are provided. In public settings, the sample is typically a liquid intended for human consumption, for example a beverage such as water, soda, or an alcoholic drink. In a forensic or diagnostic setting, the sample is typically a body fluid, for example urine, saliva, blood, serum or plasma. The GHB source can be GHB, a precursor thereto, or an analog thereof, as described more fully below.

The sample is contacted with a first oxidoreductase that can oxidize GHB present in the sample to succinic semialdehyde (SSA), while simultaneously reducing a cofactor for the oxidoreductase. The reduced cofactor is then detected, directly or indirectly. Preferably, the reduced cofactor is detected indirectly from a change in a detection reagent that can react with the reduced cofactor and undergo a detectable change. Any change in the detection reagent which can be detected can be used. For example, any change which can be detected optically, spectroscopically, photometrically, electrochemically (amperometrically, potentiometrically), thermometrically, piezoelectrically, radiographically, colorimetrically, calorimetrically and/or magnetically can be used in the disclosed methods. Preferably, the detection reagent undergoes a detectable change in absorption or emission, most preferably in the visible region. The detection reagent may be a hydride abstractor, and is preferably a chromogen or dye. Reduction of the detection reagent by the reduced cofactor is preferably mediated by a second oxidoreductase.

Positive and/or negative control samples may also be tested in conjunction with the test sample. The methods of the invention can be used in soluble form in a single reaction chamber for analysis of an individual sample or in a multiwell format where a plurality of samples is assayed simultaneously. The results are preferably assayed visually and/or spectrophotometrically. Where desired, the assay may be quantitative or semi-quantitative.

The methods can also be employed on a support, for example on a test strip. Any or all of the reagents used in the assay may be conjugated to the support, or may be deposited on the support but remain free to diffuse as permitted by the assay conditions. The support may be coupled to one or more other materials, and may be incorporated into a housing. "Dipstick" devices such as those used for testing other analytes may be used for performing the methods described herein. The support for a test sample may also include a positive control region where a reagent that will cause a detectable signal is deposited in a distinguishable pattern from the pattern produced by a GHB source in the test sample; exemplary reagents useful for forming a positive control region include GHB and a reduced cofactor. Alternatively, a support different from that for the test sample may be used for the control sample.

Multiple positive controls for various GHB sources may be simultaneously employed.

For visual assays, the results can be compared to color samples indicating the reaction results in the presence of known amounts of GHB to provide a comparative method for determining GHB concentration. Control samples containing known amounts of GHB can also be simultaneously used for direct comparison to the test sample.

Additional reagents may be included in the assay which can convert GHB precursors to forms which can act as substrates for the first oxidoreductase to allow their detection. An esterase may be included to convert esters of GHB, including internal esters such as GBL, to GHB. An amidase may be included to similarly convert amidated forms of GHB to GHB. The legal substance 1,4-butanediol can be detected with a combination of alcohol and aldehyde dehydrogenases, each of which is commercially available. A combination of an esterase, alcohol and aldehyde dehydrogenases, and first and second oxidoreductases can be used to detect all of the common GHB sources: 1,4-butanediol, gamma-butyrolactone and GHB.

A working example utilizes the enzyme GHB dehydrogenase (GHB-DH) to react with its cofactor $NAD^+$ to produce succinic semialdehyde and NADH in the presence of GHB. Neither the reactants nor the products are colored. However, NADH can be used by a second oxidoreductase such as a diaphorase to convert a chromogen to a colored product. Thus, in the presence of GHB-DH, $NAD^+$, diaphorase and a chromogen, a colored product can be obtained from GHB.

To accomplish this, the gene for a bacterial gamma-hydroxybutyrate dehydrogenase (GHB-DH) was amplified and isolated. The gene then was cloned into a vector that expresses a fusion protein comprising GHB-DH and a protein tag that facilitates purification of the fusion protein. The fusion protein was overexpressed in bacteria and purified. Finally the fusion protein, diaphorase, NAD$^+$, chromogen and pH buffer were placed onto a solid support in order to create a "dipstick" that signals the presence of GHB visually through a color change.

The invention described herein is useful for any assay in which a sample can be interrogated regarding a GHB source. Typical assays involve determining the presence of the GHB source in the sample and/or its amount. The assays may determine relative amounts, or may be quantitative or semi-quantitative, or combinations thereof.

The methods of the invention can be performed in array formats. Methods are provided for assaying 2, 3, 4, 5, 10, 15, 20, 25, 50, 100, 200, 500, 1000 or more different samples at once.

Before the present invention is described in further detail, it is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Use of the singular forms "a," "an," and "the" include plural references unless the context clearly dictates otherwise. Thus, for example, reference to "a first oxidoreductase" includes a plurality of first oxidoreductases, reference to "a support" includes a plurality of such supports, reference to "a chromogen" includes a plurality of chromogens, and the like.

Terms such as "connected," "attached," "linked," and "conjugated" are used interchangeably herein and encompass direct as well as indirect connection, attachment, linkage or conjugation unless the context clearly dictates otherwise. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

Definitions

In describing the present invention, the following terms will be employed, and are intended to be defined as indicated below.

"Cofactor" herein refers to a substance that increases an enzyme's ability to catalyze a reaction. Cofactors include metal ions and organic molecules known as coenzymes. Some cofactors are only transiently bound to enzymes, while others, known as prosthetic groups, are permanently bound to the protein. Many cofactors are derived from vitamins and minerals. Other cofactors such as coenzyme Q, lipoic acid, dolichol phosphate, biopterin, heme, and molybdopterin are synthesized in the body from simple organic compounds. Exemplary cofactors useful in the methods described herein include nicotinamide cofactors, adenine nucleotides, flavin cofactors, as well as mimetics, analogs and functional equivalents thereof.

The terms "gamma-hydroxybutyric acid," "gamma-hydroxybutyrate," "GHB", "4-hydroxybutyric acid," "oxybutyrate" and the like are used interchangeably and refer to the chemical 4-hydroxy-butanoic acid. Also encompassed by these terms are GHB analogs, salts, and isomers thereof, which are structurally related to GHB, produce a pharmacological effect like GHB, and which can be used as a substrate for a first oxidoreductase as described herein. A variety of colloquial "street names" are also used for GHB, including Soap, Scoop, Max, Liquid Ecstasy, Grievous Bodily Harm, Goop, Georgia Home Boy, Easy Lay, Cherry Meth, Everclear, Fantasy, G, G-riffic, Gamma Oh, GBH, (GBL), GHB, Jib, Liquid E, Organic quaalude, Salty water, Sleep-500, Somatomax, Vita-G, and Water.

The terms "gamma-butyrolactone," "GBL," "4-hydroxybutyric acid lactone," "1,4-butanolide," "4-butyrolactone" and the like are used interchangeably herein and refer to the chemical Dihydro-2(3H)-furanone. Also encompassed by these terms are analogs and derivatives thereof. Colloquial terms for GBL and products containing GBL include Blue Nitro Vitality, Firewater, Lactone, RenewTrient, Revivarant and Revivarant-G.

The terms "GHB source," "source of GHB" and the like refer to GHB as defined above, as well as pro-forms which can be converted to release GHB (e.g., esters or amides) and precursors to GHB, including without limitation gamma-butyrolactone, 1,4-butanediol and any other compounds which are structurally related to GHB, produce a pharmacological effect like GHB either directly or after metabolism, and which can be detected using the methods described herein either directly or after preparative steps. The precursors include those that can be used to produce GHB either chemically or after metabolism in the body.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing nonnucleotidic backbones, for example, polyamide (e.g., peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, and hybrids thereof including for example hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

Furthermore, modifications to nucleotidic units include rearranging, appending, substituting for or otherwise altering functional groups on the purine or pyrimidine base that form hydrogen bonds to a respective complementary pyrimidine or purine. The resultant modified nucleotidic unit optionally may form a base pair with other such modified nucleotidic units but not with A, T, C, G or U. Abasic sites may be incorporated which do not prevent the function of the polynucleotide. Some or all of the residues in the polynucleotide can optionally be modified in one or more ways.

"Nucleic acid probe" and "probe" are used interchangeably and refer to a structure comprising a polynucleotide, as defined above, that contains a nucleic acid sequence that can bind to a corresponding target.

"Complementary" or "substantially complementary" refers to the relationship of the sequences of different polynucleotides in terms of their ability to hybridize or base pair, for example between the two strands of a double stranded DNA molecule or between a polynucleotide primer and a primer binding site on a single stranded nucleic acid. Complementary nucleotides are, generally, A and T (or A and U), or C and G. Two single-stranded polynucleotides are said to be substantially complementary when the nucleotides of one strand, optimally aligned and compared and with appropriate nucleotide insertions or deletions, pair with at least about 80% of the nucleotides of the other strand, usually at least about 90%, and more preferably at least about 98%.

Alternatively, substantial complementarity exists when a polynucleotide will hybridize under selective hybridization conditions to another polynucleotide. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984).

"Preferential binding" or "preferential hybridization" refers to the increased propensity of one member of a binding pair to bind to a second member of a binding pair as compared to other molecules present in the sample.

Stringent hybridization conditions will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. Other factors may affect the stringency of hybridization, including base composition and length of the complementary strands, presence of organic solvents and extent of base mismatching; the combination of parameters used is more important than the absolute measure of any one alone. Other hybridization conditions which may be controlled include buffer type and concentration, solution pH, presence and concentration of blocking reagents (e.g., repeat sequences, Cot1 DNA, blocking protein solutions) to decrease background binding, detergent type(s) and concentrations, molecules such as polymers which increase the relative concentration of the polynucleotides, metal ion(s) and their concentration(s), chelator(s) and their concentrations, and other conditions known or discoverable in the art. Formulas may be used to predict the optimal melting temperature for a perfectly complementary sequence for a given probe, but true melting temperatures for a probe under a set of hybridization conditions must be determined empirically. Also, a probe may be tested against its exact complement to determine a precise melting temperature under a given set of condition as described in Sambrook et al, "Molecular Cloning," $2^{nd}$ edition, Cold Spring Harbor Laboratory Press, 1989.

Hybridization temperatures can be systematically altered for a given hybridization solution using a support associated with target polynucleotides until a temperature range is identified which permits detection of binding of a detectable probe at the level of stringency desired, either at high stringency where only target polynucleotides with a high degree of complementarity hybridize, or at lower stringency where additional target polynucleotides having regions of complementarity with the probe detectably hybridize above the background level provided from nonspecific binding to noncomplementary target polynucleotides and to the support. When hybridization is performed with potential target polynucleotides on a support under a given set of conditions, the support is then washed under increasing conditions of stringency (typically lowered salt concentration and/or increased temperature, but other conditions may be altered) until background binding is lowered to the point where distinct positive signals may be seen. This can be monitored in progress using a Geiger counter where the probe is radiolabeled, radiographically, using a fluorescent imager, or by other means of detecting probe binding. The support is not allowed to dry during such procedures, or the probe may become irreversibly bound even to background locations. Where a probe produces undesirable background or false positives, blocking reagents are employed, or different regions of the probe or different probes are used until positive signals can be distinguished from background. Once conditions are found that provide satisfactory signal above background, the target polynucleotides providing a positive signal are isolated and further characterized. The isolated polynucleotides can be sequenced; the sequence can be compared to databank entries or known sequences; where necessary, full-length clones can be obtained by techniques known in the art; and the polynucleotides can be expressed using suitable vectors and hosts to determine if the polynucleotide identified encodes a protein having similar activity to that from which the probe polynucleotide was derived. If the protein does have similar activity, it is definitively identified as a homologue.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include polypeptides containing co- and/or post-translational modifications of the polypeptide, for example, glycosylations, acetylations, phosphorylations, and sulphations. In addition, protein fragments, analogs (including amino acids not encoded by the genetic code, e.g. homocysteine, ornithine, D-amino acids, and creatine), natural or artificial mutants or variants or combinations thereof, fusion proteins, derivatized residues (e.g. alkylation of amine groups, acetylations or esterifications of carboxyl groups) and the like are included within the meaning of polypeptide.

The term "support" refers to a material having a propensity to assume a particular shape.

The term "substrate" refers to a molecule that is a reactant for an enzymatic reaction.

As used herein, the term "binding pair" refers to first and second molecules that bind specifically to each other with greater affinity than to other components in the sample. The binding between the members of the binding pair is typically noncovalent. Exemplary binding pairs include immunological binding pairs (e.g. any haptenic or antigenic compound in combination with a corresponding antibody or binding portion or fragment thereof, for example digoxigenin and anti-digoxigenin, fluorescein and anti-fluorescein, dinitrophenol and anti-dinitrophenol, bromodeoxyuridine and anti-bromodeoxyuridine, mouse immunoglobulin and goat anti-mouse immunoglobulin) and nonimmunological binding pairs (e.g., biotin-avidin, biotin-streptavidin, hormone [e.g., thyroxine and cortisol]-hormone binding protein, receptor-receptor agonist or antagonist (e.g., acetylcholine receptor-acetylcholine or an analog thereof), IgG-protein A, lectin-carbohydrate, enzyme—enzyme cofactor, enzyme—enzyme inhibitor, and complementary polynucleotide pairs capable of forming nucleic acid duplexes. One or both member of the binding pair can be conjugated to additional molecules.

The term "antibody" as used herein includes antibodies obtained from both polyclonal and monoclonal preparations, as well as: hybrid (chimeric) antibody molecules (see, for example, Winter et al. (1991) *Nature* 349:293–299; and U.S. Pat. No. 4,816,567); F(ab')2 and F(ab) fragments; Fv molecules (noncovalent heterodimers, see, for example, Inbar et al. (1972) *Proc Natl Acad Sci USA* 69:2659–2662; and Ehrlich et al. (1980) *Biochem* 19:4091–4096); single-chain Fv molecules (sFv) (see, for example, Huston et al. (1988) *Proc Natl Acad Sci USA* 85:5879–5883); dimeric and trimeric antibody fragment constructs; minibodies (see, e.g., Pack et al. (1992) *Biochem* 31:1579–1584; Cumber et al. (1992) *J Immunology* 149B:120–126); humanized antibody molecules (see, for example, Riechmann et al. (1988) *Nature* 332:323–327; Verhoeyan et al. (1988) *Science* 239:1534–1536; and U.K. Patent Publication No. GB 2,276,169, published Sep. 21, 1994); and, any functional fragments obtained from such molecules, wherein such fragments retain specific-binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. Thus, the term encompasses antibodies obtained from murine hybridomas, as well as human monoclonal antibodies obtained using human hybridomas or from murine hybridomas made from mice expressing human immunoglobulin chain genes or portions thereof. See, e.g., Cote, et al. *Monoclonal Antibodies and Cancer Therapy*, Alan R. Liss, 1985, p. 77.

"Optional" or "optionally" means that the subsequently described event or circumstance may or may not occur, and that the description includes instances where the event or circumstance occurs and instances in which it does not.

The Assay

To determine if a GHB source is present in a sample, the sample is contacted with a first oxidoreductase capable of oxidizing GHB to succinic semialdehyde under conditions appropriate for such reaction. The reaction takes place either free in solution or on a support. An oxidized cofactor for the first oxidoreductase is provided. In the presence of GHB, the first oxidoreductase oxidizes GHB while simultaneously reducing the cofactor. The appearance of the reduced cofactor indicates the presence of GHB in the sample.

Any method that can be used to detect the production of the reduced cofactor by the first oxidoreductase can be used in the various aspects of the invention to produce a signal indicating the presence and/or amount of GHB or source thereof in the sample. The reduced cofactor can be detected directly, for example spectrophotometrically. Or the reduced cofactor may be indirectly assayed for the presence of the added hydride on the cofactor after reduction. In a preferred embodiment, the signal produced from the reduced cofactor is one that is visually discernible, particularly where the assay is to be used in a field test.

One approach to indirectly detecting the reduced cofactor is to detect the transfer of a hydride that is transferred from the cofactor to a chromogen or dye to produce a detectable change. This can be accomplished either by an oxidoreductase, for example a diaphorase such as lipoic dehydrogenase, ferredoxin-NADP reductase, or lipoamide dehydrogenase, or by a synthetic electron transfer agent, such as phenazine methosulfate (PMS), 1-hydroxy-5-alkylphenazinium salts such as 1-methoxy-5-methylphenazinium methylsulfate (CAS Number: 65162-13-2, available from Dojindo, Inc.) or Meldola Blue (8-dimethylamino-2,3-benzophenoxazine).

Preferably, an enzymatic reaction is used to extract the hydride due to its speed and specificity. Preferably, a second oxidoreductase is used that can oxidize the reduced cofactor while simultaneously causing a detectable change in a chromogen. Preferably, the chromogen undergoes a visually detectable change, particularly in an assay to be performed outside a laboratory. Most preferably, the chromogen changes from colorless or nearly colorless to a deep color. Alternatively, a dye that becomes colorless when it is reduced may be used.

Suitable reaction conditions are chosen to permit the methods of the invention to be performed, including pH, buffer, ionic strength, presence and concentration of one or more salts, presence and concentration of reagents and cofactors, optional cosolvents, temperature. Suitable conditions are known in the art for certain of the enzymes, and one of skill in the art can determine suitable conditions by varying these parameters and assaying the resulting enzyme activity, as is known in the art. The assay components may be used in any amount which produces a detectable result; suitable amounts can be determined through titration experiments as is known. The first and second oxidoreductases are typically used at concentrations of at least 0.1 units per liter, more typically at least 1 unit per liter, up to concentrations of 1,000,000 units per liter or less, more typically 10,000 units per liter or less, still more typically 1,000 units per liter or less. When applied to a test strip, the oxidoreductases are typically applied in an amount of at least 0.1 µl, more typically at least 1 µl, up to 10,000 µl or less, more typically 1,000 µl or less, still more typically 100 µl or less, per 100 $cm^2$ of test strip. Micro- or nanotechniques may, of course, use smaller volumes of the assay components then are used on the test strips and dipstick devices described.

A buffer is preferably included in the assay, whether performed in solution or on a support, to ensure the pH is suitable for the assay being used. Exemplary buffers include acetate, BICINE, phthalate, borate, trichloracetate, sulfosalicylate, phosphate, tartarate, citrate, succinate, maleic acid, 2,2-bis(hydroxymethyl)-2,2',2"-nitrilotriethanol, 3,3-dimethylglutaric acid, 3-N-morpholinopropanesulfonic acid (MOPS), malonic acid, 1,3-bis tris(hydroxymethyl)methylaminopropane (Bis-TRIS), tris(hydroxymethyl)aminomethane (TRIS), tris (hydroxymethyl)aminomethane-maleic acid (TRIS-maleate), tris(hydroxymethyl)aminomethane-malonic acid (TRIS-malonate), 3-N-(trishydroxymethyl)methylamino-2-hydroxypropane hydroxypropane sulfonic acid (TAPSO), 2-(tris(hydroxymethyl)methylamino)ethanesulfonic acid (TES), 1,4-piperazinebis(ethanesulfonic acid) (PIPES), 4-morpholinoethanesulfonic acid (MES), N-2-hydroxyethylpiperazine-N'-2-ethanesulfonic acid (HEPES), sulfate, amino acids (e.g., glycine), 2-amino-2-methyl-1,3-propanediol (AMPD), imidazole, triethanolamine, N,N-bis (2-hydroxyethyl)-2-aminoethanesulfonic acid (BES), N-cyclohexyl-2-aminoethanesulfonic acid (CHES) and others apparent to one of ordinary skill in the art and combinations thereof.

Additional reagents may be included in the assay which can convert GHB precursors to forms which can act as substrates for the first oxidoreductase to allow their detection. An esterase may be included to convert esters of GHB, including internal esters such as GBL, to GHB. An amidase may be included to similarly convert amidated forms of GHB to GHB. The legal substance 1,4-butanediol can be detected with a combination of alcohol and aldehyde dehydrogenases, each of which is commercially available. A combination of an esterase, alcohol and aldehyde dehydrogenases, and first and second oxidoreductases can be used to detect all of the common GHB sources: 1,4-butanediol, gamma-butyrolactone and GHB. An additional enzyme that converts ethanol to a compound that does not act as a substrate for the first oxidoreductase can also be included.

In addition, other optional ingredients that do not materially impair the assay can be included. For example, the optional ingredients can include a compound to improve the wetting of the support and/or to stabilize components of the assay. For example, a surfactant may be used. Exemplary surfactants include nonionic, anionic or cationic surfactants, such as Triton X 100®, Tween 20® and others apparent to one of ordinary skill in the art. Exemplary anionic surfactants include long carbon chain sulfates or sulfonates, for example sodium dodecyl sulfate, dioctyl sodium sulfosuccinate and sodium dodecylbenzene sulphonate. Exemplary nonionic surfactants include an octoxynol, a nonoxynol or an ethoxylated fatty alcohol. The surfactant can be included in the assay in a concentration of from 0 mM to about 200 mM, and preferably in a concentration of from about 50 mM to about 200 mM. For assays performed on a test strip, the surfactants may be used in a concentration such that a solution having an activating concentration of agent from 0.001 to 20%, preferably from 0.01 to 5%, is used in an amount of from 0.1 to 10,000 µl, preferably from 1 to 1,000 µl, more preferably from 1 to 100 µl, per 100 $cm^2$ of the test strip. Surfactants can also assist in providing a smooth color distribution for assays performed on a support; surfactants that solubilize the colored reaction product from the support are avoided in such implementations, however.

The assay optionally can include other agent(s) that improve the stability of the assay, and/or that improve the uniformity of the change which is detected. The agent(s) include polymeric agents and nonpolymeric agent(s). Exemplary polymeric agents include polyvinylpyrrolidone, polyvinyl alcohol, gum arabic, gelatin, algin, carrageenan, casein, albumin, methyl cellulose, uncapped polyethylene glycol, end-capped polyethylene glycol, polysaccharides (e.g., sucrose) and other natural and synthetic polymeric materials and combinations thereof. Exemplary nonpolymeric agents include monosaccharides (e.g., glucose) and glycerol. Individual reagents for performing the assay (e.g., enzymes) may contain such stabilizing agents, or solutions comprising multiple reagents for performing the assay may be provided and may comprise such agent(s).

In addition, to improve the color resolution and differentiation of the color transition in the assay, inert background dyes can be included as described for example in U.S. Pat. Nos. 4,351,899 and 5,510,245. This can be useful with highly colored samples (e.g.). For example, a pink background dye could be used in an assay on a red sample, and a chromogen that is converted to black could be used for detection. Also, a sample-decolorizing agent can be included which decreases the color in the sample prior to performance of the enzymatic detection assay. The decolorizing treatment should not impair the detection of GHB, either through masking or removing the GHB source or by adversely affecting other components of the assay. Thus the decolorizing treatment either does not use reagents which adversely affect components of the assay or removes or destroys such reagents before the assay is performed. Exemplary oxidizing agents that may be used as decolorizing agents include hydrogen peroxide, carbamide peroxide, and bleach.

Nonaqueous solvents may be included to solubilize components of the assay as needed. Exemplary solvents include isopropyl alcohol, acetone, dimethylformamide, dimethylsulfoxide, acetonitrile, and others known in the art, and combinations thereof. The solvents are soluble or miscible with aqueous solutions at least to the extent necessary to perform the assay. It may be desirable to avoid solvents containing primary alcohol groups to reduce the background produced by the assay in the absence of GHB, as compounds containing primary alcohol groups can be utilized as alternative substrates by certain oxidoreductases that can oxidize GHB to SSA.

Other optional components in the assay include proteins, for example bovine serum albumin, saccharides such as maltose, glucose, sucrose, glycerol and the like, high molecular weight compounds such as polyethylene glycol and others known in the art and metal ions, for example magnesium, potassium, calcium and others known in the art. These metal ions may also act as enzyme activators. Chelating compounds such as ethyleneglycol bis-(beta-aminoethyl ether) tetraacetic acid (EGTA) may also optionally be used. These optional components may be used in a concentration such that a saccharide solution having a saccharide concentration of from 0.1 to 50% preferably from 1 to 25%), a protein solution having a protein concentration of from 0.001 to 50% (preferably from 0.1 to 25%), a metal ion solution having a metal i on concentration of from 0.001 to 10 mM (preferably from 0.1 to 10 mM), EGTA solution having an EGTA concentration of from 0.001 to 10 mM (preferably from 0.1 to 2 mM), is used in an amount of from 0.1 to 10,000 $\mu$l, preferably from 1 to 1,000 $\mu$l, more preferably from 1 to 100 $\mu$l, per 100 $cm^2$ of a test strip. Where the assay employs an enzyme comprising or otherwise requiring metal cofactors, chelating agents that chelate those metals are avoided, however. Where the assay employs a first oxidoreductase that can bind to or otherwise act on a saccharide or primary alcohol in a manner which adversely affects the ability to detect the signal produced when GHB is present in the sample, such saccharide or other primary alcohol is desirably avoided.

A hemoglobin suppressor can optionally be used to decrease the nonenzymatic dye-forming reaction between hemoglobin and a tetrazolium compound for those samples containing hemoglobin or other heme-containing group(s), as described in U.S. Pat. No. 5,902,731. Preferred hemoglobin suppressors include nitrites, particularly as the potassium and sodium nitrite salts.

After the reaction has progressed for a suitable period of time, the reaction may be quenched, for example by contacting the first and/or second oxidoreductases with a solution which inactivates them, for example by denaturation. This can be done in order to prevent nonpreferred substrates of the enzyme(s) which may be present in the sample from producing a false positive upon prolonged development. An assay utilizing *R. eutropha* SSA reductase as the first oxidoreductase and *B. stearothermophilus* diaphorase as the second oxidoreductase may be quenched for example using a solution of 10% acetic acid.

The Sample

In principle, the sample can be any substance suspected of comprising a GHB source, particularly a liquid or solid. The sample may include those forms in which the GHB source is typically provided or abused, including without limitation: a bottled liquid; a comestible such as a food product; a drink in any form; a beverage, including water; liquid, anabolic, dietary or nutritional supplements; oils; extracts; elixirs; pharmaceutical preparations; natural product preparations; nutraceuticals; etc. The sample may be a comestible that is suspected of having been adulterated with a GHB source, or a forensic or clinical sample from a subject suspected of ingesting a GHB source. The beverage may be an ethanol-containing beverage, for example beer, wine, a mixed drink, a liqueur, or a more concentrated form, typically containing at least 40% ethanol, such as vodka, gin, rum, whiskey, etc.

The sample can be any source of biological material that can be obtained from a living organism directly or indirectly, including cells, tissue or fluid, and the deposits left by that organism. Nonlimiting examples of the sample include: blood; urine; tears; saliva; semen; milk; sputum; mucus; plasma; serum; spinal fluid; lymph fluid; the external secretions of the skin, respiratory, intestinal, and genitourinary tracts; a buccal swab; a vaginal swab; a rectal swab; an aspirate; a needle biopsy; a section of tissue obtained for example by surgery or autopsy; tumors; and organs.

Test samples having unknown amounts of GHB sources from substances to be tested will typically be used. The methods can also be performed using samples that are positive control samples known to contain a GHB source or a surrogate therefor, as well as negative control samples known to lack a GHB source that can be used to determine whether a given set of assay conditions produces false positive results (a positive signal even in the absence of a GHB source in the sample).

The sample can be diluted, dissolved, suspended, extracted, heated or otherwise treated to solubilize, purify and/or concentrate any GHB source present in the sample or to render it accessible to reagents that are used in the methods described herein or to improve the performance of the methods disclosed. The sample can be any portion or all of the substance that is suspected of comprising a GHB source. Typically, the sample is obtained as or dispersed in a predominantly aqueous medium. Dilutions may be made from the initial sample, particularly where quantitative assays are being performed, or where it is otherwise desirable to dilute the sample, for example to dilute out an interfering substance. The silica extraction methods described in U.S. Pat. No. 6,156,431 maybe used in conjunction with performing the enzymatic methods disclosed. The sample may also be treated to inactivate, deplete or dilute substances that would otherwise adversely affect the methods described herein. For example, where the sample comprises heme groups, a nitrite can be used as described in U.S. Pat. No. 5,902,731 to prevent the heme groups from adversely affecting the enzymatic methods. Where the sample comprises an aqueous solution containing ethanol, evaporation to dryness or treatment with an enzyme selective for ethanol can be used to remove or destroy the ethanol to prevent it from producing a false positive result.

The First Oxidoreductase

The first oxidoreductase is a polypeptide comprising an enzymatic activity that can oxidize 4-hydroxybutyric acid to succinic semialdehyde while simultaneously reducing a cofactor. The first oxidoreductase may perform this oxidation through either a "forward" or "reverse" reaction, operating either in the direction normally predominant in its typical metabolic setting in its host source, or in the opposite or "reverse" direction. For example, a succinic semialdehyde reductase that normally converts succinic semialdehyde to 4-hydroxybutyrate in a host organism can be used to catalyze the reverse reaction and convert 4-hydroxybutyrate present in the test sample to succinic semialdehyde, at least to the point of equilibrium under the assay conditions.

Any polypeptide that can oxidize gamma-hydroxybutyrate and/or reduce succinic semialdehyde using a reducible cofactor can be used as the first oxidoreductase. Exemplary classes of polypeptides useful in this regard include succinic semialdehyde reductases, glucuronate reductases, aflatoxin aldehyde reductases, and gamma-hydroxybutyrate dehydrogenases (including 4-hydroxybutyrate dehydrogenases and other). Glucuronate reductases have been shown to have GHB dehydrogenase/SSA reductase activity (Kaufman and Nelson, 1981; Cromlish and Flynn, 1985; Kaufman and Nelson, 1991; Nelson and Kaufman, 1994). Aflatoxin aldehyde reductase has also been shown to reduce succinic semialdehyde (Ellis and Hayes, 1995). Exemplary sources of these classes of polypeptides include those organisms that have been shown to contain such enzymatic activity, to contain a protein homologous to an enzyme known to have such activity, or to contain a polynucleotide encoding a predicted protein with homology to an enzyme known to have such activity. The first oxidoreductase may be provided in any active form for performing the methods described herein, for example in the form of a crude lysate obtained from a source organism, as a purified formulation obtained from a source organism, or as a lysate or purified formulation from a host cell expressing a coding sequence for such an enzyme, including in the form of a fusion protein.

Appropriate enzymatic activity of predicted or uncharacterized proteins for use in this invention can be determined using any suitable technique; a number of techniques are known in the art, and the methods described herein can be used. For example, an expression vector comprising a cloned coding sequence for such a predicted protein may be tested for its ability to confer the ability to grow on a medium using 4-hydroxybutyric acid as a carbon source to a host cell, or for its ability to add an enzymatic activity to a protein lysate from a host cell normally lacking such activity by testing such protein lysate in an enzymatic assay for the ability to oxidize GHB. It is to be expected that there may be some redundancy among enzymes and predicted proteins listed below that are from the same source organism. Additionally, although some of these proteins may have been initially characterized as having one such enzymatic activity listed below or as being related to an enzyme known to have such activity, the enzymes may possess more than one of the activities recited. Accession numbers which can be used to retrieve the protein sequence, or in some cases the coding sequence, from the U.S. National Center for Biotechnology Information (NCBI; National Library of Medicine, Building 38A, Bethesda, Md. 20894) and reference(s) describing the enzymatic activity are provided in parentheses following the organism name, along with the location of coding regions and gene abbreviations.

Exemplary source organisms comprising succinic semialdehyde (SSA) reductase activity, a protein homologous to a known succinic semialdehyde reductase and/or a coding sequence for a predicted protein homologous to a known succinic semialdehyde reductase include *Arabidopsis thaliana* (AY044183).

Exemplary source organisms comprising glucuronate reductase activity, a protein homologous to a known glucuronate reductase and/or a coding sequence for a predicted protein homologous to a known glucuronate reductase include *Clostridium acetobutylicum* (NC_003030 cds 1718822.1719937/gene="CAC1574"), *Clostridium perfringens* (NC_003366 cds 668530.669645/gene="CPE0539"), hamster (Kaufman and Nelson, 1981), pig (Cromlish and Flynn, 1985), and rat (Nelson and Kaufman, 1994).

Exemplary source organisms comprising aflatoxin aldehyde reductase activity, a protein homologous to a known aflatoxin aldehyde reductase and/or a coding sequence for a predicted protein homologous to a known aflatoxin aldehyde reductase include *Danio rerio* (BI868074), *Gallus gallus* (BM490659), *Homo sapiens* (XP_066911), *Mus musculus* (BG276960), *Neurospora crassa* (AI392098), *Rattus norvegicus* (P38918; Ellis and Hayes, 1995), *Saccharomyces bayanus* (AL399499), and *Xenopus laevis* (BG348484).

Exemplary source organisms comprising gamma-hydroxybutyrate dehydrogenase activity, a protein homologous to a known gamma-hydroxybutyrate dehydrogenase and/or a coding sequence for a predicted protein homologous to a known gamma-hydroxybutyrate dehydrogenase include Alcaligenes eutrophus (*Ralstonia eutropha*; nucleotide L36817; protein 139568), *Arabidopsis thaliana* (AAK94781), *Brucella melitensis* (NP_542072), *Clostridium acetobutylicum* (NP_348201), *Clostridium aminobutyricum* (CAB60037), *Clostridium kluyveri* (P38945), *Clostridium perfringens* (NP_561455), *Homo sapiens* (AA995974), *Mesorhizobium loti* (NP_104263), *Mus musculus* (AA403499), *Mycobacterium tuberculosis* (NC_000962 cds 193115.193570/gene="Rv0163"), *Ralstonia solanacearum* (NP_519892), Uncultured bacterium AH1 (AAD55929), Uncultured bacterium AH5 (AAD55928), and Uncultured bacterium AH6 (AAD55930).

Also encompassed are those oxidoreductases that possess such activity and are homologous to the exemplary first oxidoreductases recited above or are encoded by polynucleotides whose complement can hybridize to the polynucleotides encoding the exemplary first oxidoreductases. These oxidoreductases include naturally occurring homologues from other species, functional equivalents thereof, as well as synthetically prepared proteins based on such enzymes, whether through fusions among known coding sequences, recombinations therefrom, mutagenesis thereof including mutagenesis scans, any form of molecular evolution, etc.

Once a desired genomic or cDNA for a first oxidoreductase has been isolated, it can be sequenced by known methods. It is recognized in the art that such methods are subject to errors, such that multiple sequencing of the same region is routine and is still expected to lead to measurable rates of mistakes in the resulting deduced sequence, particularly in regions having repeated domains, extensive secondary structure, or unusual base compositions, such as regions with high GC base content. When discrepancies arise, resequencing can be done and can employ special methods. Special methods can include altering sequencing conditions by using: different temperatures; different enzymes; proteins that alter the ability of oligonucleotides to form higher order structures; altered nucleotides such as ITP or methylated dGTP; different gel compositions, for example adding formamide; different primers or primers located at different distances from the problem region; or different templates such as single-stranded DNAs. Sequencing of mRNA also can be employed.

For the most part, some or all of the coding sequence for the polypeptide having oxidoreductase activity is from a natural source. In some situations, however, it is desirable to modify all or a portion of the codons, for example, to enhance expression, by employing host-preferred codons. Host-preferred codons can be determined from the codons of highest frequency in the proteins expressed in the largest amount in a particular host species of interest. Thus, the coding sequence for a polypeptide having oxidoreductase activity can be synthesized in whole or in part. All or portions of the polynucleotide also can be synthesized to remove any destabilizing sequences or regions of secondary structure that would be present in the transcribed mRNA. All or portions of the polynucleotide also can be synthesized to alter the base composition to one more preferable in the desired host cell. Methods for synthesizing sequences and bringing sequences together are well established in the literature. In vitro mutagenesis and selection, site-directed mutagenesis, or other means can be employed to obtain mutations of naturally occurring oxidoreductase genes to produce a polypeptide having oxidoreductase activity in vivo with more desirable physical and kinetic parameters for function in the host cell, such as a longer half-life or a higher activity.

Other polynucleotides also can be used that are substantially identical to known oxidoreductase coding sequences, or that encode polypeptides which are substantially identical to known oxidoreductases, and that encode proteins having the desired activity. By substantially identical is intended an amino acid sequence or nucleic acid sequence exhibiting in order of increasing preference at least 60%, 70%, 75%, 80%, 85%, 90%, 95% or greater "homology" (or "identity") to the known oxidoreductases having the desired selectivity. For polypeptides, the length of comparison sequences generally is at least 16 amino acids, preferably at least 20 amino acids, or most preferably 35 amino acids. For nucleic acids, the length of comparison sequences generally is at least 50 nucleotides, preferably at least 60 nucleotides, and more preferably at least 75 nucleotides, and most preferably, 110 nucleotides. Homology typically is measured using sequence analysis software, for example, the Sequence Analysis software package of the Genetics Computer Group, University of Wisconsin Biotechnology Center, 1710 University Avenue, Madison, Wis. 53705, MEGAlign (DNAStar, Inc., 1228 S. Park St., Madison, Wis. 53715), and MacVector (Oxford Molecular Group, 2105 S. Bascom Avenue, Suite 200, Campbell, Calif. 95008). Such software matches similar sequences by assigning degrees of homology to various substitutions, deletions, and other modifications. Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, J. Mol. Biol. 157: 105–132, 1982), on the basis of the ability to assume similar polypeptide secondary structure (Chou and Fasman, Adv. Enzymol. 47: 45–148, 1978), on similarity in space-filling characteristics, or on the basis of combinations of such parameters with each other and/or with additional parameters. Polynucleotides may also be used that encode naturally occurring oxidoreductases having the desired selectivity and having normalized alignment scores with the disclosed oxidoreductases with values at least 3, 4, 5, 6, 7, 8, 9 or 10 standard deviations above random (Doolittle, Protein Sci. 1:191–200, 1992; Doolittle et al., Cold Spring Harbor Symp. 51:447–455, 1986), along with variants, homologues and mutants thereof as described herein and having such selectivity.

Encompassed by the present invention are related oxidoreductases from the same or other organisms having the desired selectivity for oxidizing GHB to SSA. Such related oxidoreductases include variants of known naturally occurring enzymes within the same or different species as well as homologues of the known oxidoreductases from other species.

The regions of an oxidoreductase polypeptide important for oxidoreductase activity can be determined through routine mutagenesis, expression of the resulting mutant polypeptides and determination of their activities. Mutants may include deletions, insertions and point mutations, or combinations thereof. A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR.

Chemical mutagenesis also can be used for identifying regions of an oxidoreductase polypeptide important for activity. A mutated construct is expressed, and the ability of the resulting altered protein to function as an oxidoreductase is assayed. Such structure-function analysis can determine which regions may be deleted, which regions tolerate insertions, and which point mutations allow the mutant protein to function in substantially the same way as the native oxidoreductase. All such mutant proteins and nucleotide sequences encoding them are within the scope of the present invention.

Also encompassed by the invention are purified and/or isolated forms of the enzymes described above, including recombinant forms as well as recombinant fusion proteins made there from.

Of particular interest is a first oxidoreductase that is a recombinant fusion protein comprising a catalytically active portion of an enzyme that can oxidize GHB to SSA and a heterologous polypeptide, wherein the first oxidoreductase is active either as the fusion protein or upon separation from the heterologous protein, for example from chemical or enzymatic cleavage of a native or introduced linking group joining the first oxidoreductase to the heterologous protein.

The oxidoreductase or a modified oxidoreductase coding sequence may be ligated to a heterologous sequence to encode a fusion protein. The fusion protein may be engineered to contain a cleavage site located between the oxidoreductase sequence and the heterologous protein sequence, so that the oxidoreductase can be separated from the heterologous moiety.

The use of chimeric or "fusion" or "tagged" proteins, i.e., those that contain a functional domain (catalytic or otherwise) together with a binding domain, can be particularly useful in protein purification methods. For example, the glutathione S-transferase gene fusion system is designed to express a gene of interest fused to the C-terminal of glutathione S-transferase. The recombinant protein is purified by affinity chromatography using a glutathione-Sepharose column.

Another example is the Protein-A gene fusion vector that permits a high level of expression of fusion proteins in both *E. coli* and *Staphylococcus aureus* cells (B. Nilsson, et al. (1985) EMBO J. 4(4):1075–1080). The IgG binding domain of Protein A provides a rapid purification method of the fusion protein using IgG-conjugated columns. Similar systems have been developed based on: beta-galactosidase fusion proteins purified on IPTG-Sepharose or metal chelate chromatography; histidine hexamer fusion proteins purified using metal chelate chromatography; maltose-binding protein fusion proteins purified on maltose-conjugated columns; and epitope-tagged proteins purified using antibodies to the epitope, including the myc-tag system (Kaufman R. J. et al., 1987, EMBO J.6:187–193) and the hemagglutinin tag system (Herrscher, R. F. et al (1995) Genes Dev. 9:3067–3082).

A working example of a fusion protein comprising a functionally active *R. eutropha* SSA reductase is provided (Examples 1–4). The GST fusion protein system was found to provide an enzymatically active fusion protein comprising the *R. eutropha* SSA reductase in high yield. Prior efforts to express and purify the R. eutropha SSA reductase in the histidine-tag system resulted in an inactive protein being formed, apparently due to the chelating properties of the histidine tag.

In accordance with the invention, nucleotide sequences that encode oxidoreductases, fragments, fusion proteins or functional equivalents thereof, may be used to generate recombinant polynucleotides that direct the expression of the oxidoreductase, or a functionally active peptide, fusion protein or functional equivalent thereof, in appropriate host cells.

Once a polynucleotide encoding the desired oxidoreductase has been obtained, it is placed in a vector capable of replication in a host cell, or is propagated in vitro by means of techniques such as PCR or long PCR. Replicating vectors can include plasmids, phage, viruses, cosmids and the like. Desirable vectors include those useful for mutagenesis of the gene of interest or for expression of the gene of interest in host cells, which may be the same as or different than the host cell used for propagation. The technique of long PCR has made in vitro propagation of large constructs possible, so that modifications to the gene of interest, such as mutagenesis or addition of expression signals, and propagation of the vectors can occur entirely in vitro without the use of a replicating vector or a host cell.

The invention also includes a host cell comprising a nucleic acid construct of the invention. In a preferred embodiment, a recombinant host cell is provided that comprises at least one copy of a polynucleotide which encodes a functionally active oxidoreductase or fusion protein thereof, wherein the cell or an ancestor of the cell was transformed with a vector comprising said DNA sequence. The nucleic acid construct may desirably be an expression vector wherein the polynucleotide is operably linked to transcriptional and translational control sequences functional in the desired host cell.

Host cells are manipulated to express a polynucleotide encoding a polypeptide(s) that catalyzes the conversion of GHB to SSA. To achieve expression, the transformed DNA is operably associated with transcriptional and translational initiation and termination regulatory regions that are functional in the host cell. Constructs comprising the gene to be expressed can provide for integration into the genome of the host cell or can autonomously replicate in the host cell.

For expression of an oxidoreductase polypeptide, functional transcriptional and translational initiation and termination regions are operably linked to the polynucleotide encoding the oxidoreductase polypeptide. Expression of the polypeptide-coding region can take place in vitro or in a host cell. Transcriptional and translational initiation and termination regions are derived from a variety of nonexclusive sources, including the polynucleotide to be expressed, genes known or suspected to be capable of expression in the desired system, expression vectors, chemical synthesis, or from an endogenous locus in a host cell. Additionally, in order to produce a recombinant fusion protein, the heterologous coding sequence to be fused to the oxidoreductase coding sequence may be introduced into a native locus for that oxidoreductase at the proper location, for example via homologous recombination.

In vitro expression can be accomplished, for example, by placing the coding region for the oxidoreductase polypeptide in an expression vector designed for in vitro use and adding rabbit reticulocyte lysate and cofactors; labeled amino acids can be incorporated if desired. Such in vitro expression vectors may provide some or all of the expression signals necessary in the system used. These methods are well known in the art and the components of the system are commercially available. The reaction mixture can then be assayed directly for the polypeptide, for example by determining its activity, or the synthesized polypeptide can be purified and then assayed.

Expression in a host cell can be accomplished in a transient or stable fashion. Transient expression can occur from introduced constructs that contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, integration of constructs can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

When increased expression of the oxidoreductase polypeptide in the source organism is desired, several methods can be employed. Additional genes encoding the oxidoreductase polypeptide can be introduced into the host organism. Expression from the native oxidoreductase locus also can be increased through homologous recombination, for example by inserting a stronger promoter into the host genome to cause increased expression, by removing destabilizing sequences from either the mRNA or the encoded protein by deleting that information from the host genome, or by adding stabilizing sequences to the mRNA (U.S. Pat. No. 4,910,141).

Constructs comprising the gene of interest may be introduced into a host cell by any suitable technique. Typical techniques include transformation, protoplast fusion, lipofection, transfection, transduction, conjugation, infection, bolistic impact, electroporation, microinjection, scraping, or any other method that introduces the gene of interest into the host cell. For convenience, a host cell that has been manipulated by any method to take up a DNA sequence or construct will be referred to as "transformed" or "recombinant" herein.

The subject host will have at least have one copy of the expression construct and may have two or more, depending upon whether the gene is integrated into the genome, amplified, or is present on an extrachromosomal element having multiple copy numbers.

The recombinant host cell can be identified by selection for a marker contained on the introduced construct. Alternatively, a separate marker construct may be introduced with the desired construct, as many transformation techniques introduce multiple DNA molecules into host cells. Typically, recombinant hosts are selected for their ability to grow on selective media. Selective media may incorporate an antibiotic or lack a factor necessary for growth of the untransformed host, such as a nutrient or growth factor. An introduced marker gene therefore may confer antibiotic resistance, or encode an essential growth factor or enzyme, and permit growth on selective media when expressed in the recombinant host. Selection of a recombinant host also can occur when the expressed marker protein can be detected, either directly or indirectly. The marker protein may be expressed alone or as a fusion to another protein. The marker protein can be detected by its enzymatic activity; by its light-producing or modifying characteristics. "Hit and run" techniques may also be used.

Prokaryotic host cells of interest include those of the genera Eschericia, Bacillus, Lactobacillus, and Cyanobacter. Eukaryotic host cells include mammalian cells, avian cells such as of chickens, and other cells amenable to genetic manipulation including insect, fungal, and algae cells. The cells may be cultured or formed as part or all of a host organism including an animal. Viruses and bacteriophage also may be used with the cells, particularly for gene transfer, cellular targeting and selection.

Exemplary host fungi include Saccharomyces cerevisiae, Saccharomyces carlsbergensis, or other yeast such as Schizosaccharomyces, Candida, Kluyveromyces, Pichia or other fungi, for example, filamentous fungi such as Aspergillus, Neurospora, Penicillium, etc.

Production of protein in insect cells can be conducted using baculovirus expression vectors. Transgenic marine algae may be prepared as described in U.S. Pat. No. 5,426,040.

The transformed host cell is grown under appropriate conditions adapted for the desired end result. Media conditions that may be optimized include: carbon source, nitrogen source, addition of substrate, final concentration of added substrate, form of substrate added, aerobic or anaerobic growth, growth temperature, inducing agent, induction temperature, growth phase at induction, growth phase at harvest, pH, density, and maintenance of selection.

Purification of the native protein or a derivative or functional equivalent thereof can be accomplished through methods known in the art. Proteins that are produced in the host cell in a form which is secreted into the culture medium and/or the periplasmic space of bacteria can be purified from the culture medium itself either directly or after removal of the cell wall. Proteins that are produced in the host cell in an intracellular form can be obtained by lysing the host cell. Any method of lysis that allows purification of sufficient protein in an acceptably functional form can be used; exemplary lysis methods include the use of detergents, sonication, physical methods (e.g., french press), heating, exposure to hypoosmotic conditions, etc. The medium containing the protein can then be subjected to additional procedures as desired to further purify and/or isolate the protein; exemplary methods include salt precipitation, any of the various methods of column chromatography (e.g., cation exchange, anion exchange, size exclusion, affinity, etc.), isoelectric focusing, gel purification, centrifugation, affinity purification methods (e.g., based on binding to a substrate, a cofactor, a binding partner, an antibody, etc.), HPLC, dialysis, etc.

An oxidoreductase of particular interest is the SSA reductase from R. eutropha (also referred to as a GHB dehydrogenase or GHB-DH, for its activity in the reverse reaction). The gene has been sequenced and the substrate selectivity of the protein investigated (yalentin, 1995). See FIGS. 1 and 2. Examples of the methods described herein have been provided using this oxidoreductase, which has been found to provide rapid and sensitive results.

The Cofactor

The cofactor is one that, in oxidized form, increases the ability of the first oxidoreductase to oxidize GHB; the oxidized cofactor is simultaneously reduced in this reaction. Where a second oxidoreductase is used, the reduced cofactor thus produced is one that can serve as a cofactor for the second oxidoreductase.

Cofactors useful in the methods described herein include nicotinamide cofactors, flavin cofactors, quinone cofactors and oxoacids. Exemplary nicotinamide cofactors include nicotinamide adenine dinucleotide (NAD), nicotinamide adenine dinucleotide phosphate (NADP), nicotinamide 1,N6-ethenoadenine dinucleotide, and nicotinamide 1,N6-ethenoadenine dinucleotide phosphate. Flavin cofactors include those cofactors comprising a flavin group or an active portion thereof. Exemplary flavin cofactors include riboflavin, isoalloxazine, flavin mononucleotide (FMN), and flavin adenine dinucleotide (FAD). Quinone cofactors include those cofactors comprising a quinone group. Exemplary quinone cofactors include pyrroloquinoline quinone (PQQ). Exemplary oxoacids include alpha-ketoglutarate.

Also encompassed are analogs of natural cofactors that can be used with at least one oxidoreductase in performing the methods described herein. For example, analogs of $NAD^+$ are described in: Zateman et al., J. Biol. Chem. 209:453 (1954); Zateman et al., J. Biol. Chem., 209:467 (1954); Kaplan et al., J. Biol. Chem. 221:823, 833 (1956); "The Pyridine Nucleotide Coenzymes" by J. Everse, B. Anderson and W-S. You, Academic Press, New York, 1982, pp 92–132; "Pyridine Nucleotide Coenzymes" (Coenzymes and Cofactors, Vol III), John Wiley, New York, 1987, pp 324–365; Biellman et al., FEBS Lett. 7:199 (1970); Lamos et al., U. S. Pat. No. 5,037,738; Modrovich, U.S. Pat. No. 4,394,449; U.S. Pat. No. 5,766,874 and U.S. Pat. No. 5,801,006. Exemplary NADPH and NADH cofactor analogs include 3-acetylpyridine adenine dinucleotide or 3-acetylpyridine-NADH; 3-acetylpyridine adenine dinucleotide phosphate or 3-acetylpyridine-NADPH; 3-pyridinealdehyde adenine dinucleotide or 3-pyridinealdehyde-NADH; 3-pyridinealdehyde adenine dinucleotide phosphate or 3-pyridinealdehyde-NADPH; thionicotinamide adenine dinucleotide or thionicotinamide-NADH; and thionicotinamide adenine dinucleotide phosphate or thionicotinamide-NADPH.

Where the *R. eutropha* SSA reductase of interest is used, preferred oxidized cofactors include $NAD^+$ and $NADP^+$.

The cofactor may be used in any amount that produces a detectable result. For example, a solution having a cofactor concentration of from 0.1 to 100 mM, preferably from 0.1 to 20 mM, can be used in an amount of from 0.1 to 10,000 µl, preferably from 1 to 1,000 µl, more preferably from 1 to 100 µl, per 100 $cm^2$ of a test strip upon which the assay is performed.

The Hydride Abstractor

A hydride abstractor is preferably used to extract a hydride from the reduced cofactor produced by the action of the first oxidoreductase in the presence of GHB in the sample. Exemplary hydride abstractors include enzymatic hydride abstractors such as oxidoreductases which can oxidize the reduced cofactor produced by the first oxidoreductase, and synthetic electron transfer agents. Exemplary enzymatic hydride abstractors include diaphorases such as lipoic dehydrogenase, ferredoxin-NADP reductase, and lipoamide dehydrogenase. Exemplary synthetic electron transfer agents include phenazine methosulfate (PMS), 1-hydroxy-5-alkylphenazinium salts (e.g., 1-methoxy-5-methylphenazinium methylsulfate, CAS Number: 65162-13-2, available from Dojindo, Inc.) and Meldola Blue (8-dimethylamino-2,3-benzophenoxazine).

Preferably, an enzymatic reaction is used to extract the hydride due to its speed and specificity. Preferably, a second oxidoreductase is used which can oxidize the reduced cofactor while simultaneously causing a detectable change in a chromogen. The hydride abstractor is used in any amount which produces a detectable result; suitable amounts can be determined empirically for a given assay format as described herein and are known in the art.

The Second Oxidoreductase

The second oxidoreductase can be any enzyme that can oxidize the reduced cofactor produced by the activity of the first oxidoreductase in the presence of GBH, and simultaneously detectably convert the chromogen. The enzyme may perform this oxidation through either a "forward" or "reverse" reaction, operating either in the direction normally predominant in its typical metabolic setting in its host source, or in the opposite or "reverse" direction.

Exemplary classes of enzymes useful in this regard include diaphorases, cytochrome b-5 reductases, aflatoxin aldehyde reductases, NAD(P)H:menadione oxidoreductases, and flavin reductases. Exemplary sources of these enzymes include those organisms that have been shown to contain either such enzyme activity or have a databank entry encoding a predicted protein with homology to an enzyme known to have such activity. Appropriate enzymatic activity of predicted proteins for use in this invention can be determined using any suitable technique; a number of techniques are known in the art, and the methods described herein can also be used. It is to be expected that there may be some redundancy among enzymes and predicted proteins listed below from the same source organism.

Exemplary source organisms comprising either diaphorase activity or a coding sequence for a predicted protein homologous to a known diaphorase include *Anabaena variabilis, Anacystis nidulans, Bacillus stearothermophilus, Bos taurus, Gallus gallus, Homo sapiens, Mus musculus, Prochlorothrix hollandica*, and *Rattus norvegicus*.

Exemplary source organisms comprising either cytochrome b-5 reductase activity or a coding sequence for a predicted protein homologous to a known cytochrome b-5 reductase include *Bos taurus, Gallus gallus, Homo sapiens*, and *Mus musculus*.

Exemplary source organisms comprising either NAD(P) H:menadione oxidoreductase activity or a coding sequence for a predicted protein homologous to a known NAD(P) H:menadione oxidoreductase include *Aeropyrum pernix, Bacillus halodurans, Danio rerio, E. coli, Gallus gallus, Giardia intestinalis,* Halobacterium sp. NRC-1, *Helicobacter pylori, Homo sapiens, Methanobacterium thermoautotrophicum, Mus musculus, Pseudomonas aeruginosa, Rattus norvegicus,* Rhizobium sp. NGR234, *Salmonella enterica, Salmonella typhimurium, Thermotoga maritime*, and *Vibrio cholerae*.

Exemplary source organisms comprising either flavin reductase activity or a coding sequence for a predicted protein homologous to a known flavin reductase include *Bacillus subtilis, Bos taurus, Danio rerio, Escherichia coli, Homo sapiens, Mus musculus, Mycobacterium leprae, Paenibacillus polymyxa, Photobacterium leiognathi, Rhodococcus erythropolis, Sacharomyces pombe, Salmonella enterica, Salmonella typhimurium, Sinorhizobium meliloti, Streptomyces coelicolor, Vibrio fischeri, Xenopus laevis,* and *Yersinia pestis*.

Preferred second oxidoreductases include those that can utilize tetrazolium chromogens as chromogens and convert them to detectable formazan dyes in the presence of the reduced cofactor under assay conditions. Appropriate assay conditions for the second oxidoreductase can be determined as described for the first oxidoreductase. It may be desirable to simultaneously determine assay conditions that are suitable for the activity of both the first and second oxidoreductases by varying assay parameters in the presence of both enzymes and their substrates.

Also encompassed are those oxidoreductases having such activity and that are homologous to the exemplary second oxidoreductases recited above, and/or that are encoded by polynucleotides whose complement can hybridize to the polynucleotides encoding the exemplary second oxidoreductases. These oxidoreductases include naturally occurring homologues from other species, functional equivalents thereof, as well as synthetically prepared proteins based on such enzymes, whether through fusions among known coding sequences, recombinations thereof, mutagenesis thereof including mutagenesis scans, any form of molecular evolution, etc.

A second oxidoreductase of particular interest where the reduced cofactor is NAD(P)H is *B. stearothermophilus* diaphorase, due to its stability, activity and availability.

The Chromogen or Dye

Chromogens and dyes useful in the methods disclosed herein include any substance that can be detectably converted by the hydride abstractor in the presence of the reduced cofactor. The chromogen may be fluorescent or luminescent, including the fluorescent chromogens described in U.S. Pat. No. 5,912,139, as well as some tetrazolium salts.

Preferably, the chromogen undergoes a visually detectable change, particularly in an assay to be performed outside a laboratory. Most preferably, the chromogen changes from colorless or nearly colorless to a deep color. Alternatively, a dye that is colored and becomes colorless may be used.

The product produced upon action of the hydride abstractor on the chromogen may be soluble or insoluble. Depending on the assay format, the chromogen or dye may be provided free in solution, conjugated to a support, impregnated in a support and/or deposited on a support.

For quantitative assays in solution or for assays using light absorbance in the detection method, for example in a multiwell tray setting, soluble reaction products are preferred so as to avoid errors introduced by the scattering of light from deposited insoluble products. For assays on porous supports such as filters and membranes, it can be desirable for the reaction products to be insoluble to facilitate deposition on the support.

Exemplary chromogens include methyl blue, 2,6-dichlorophenolindophenol, resazurin, $Fe^{III}$-phenanthroline complex, alamar blue, the thiol-responsive indicator dyes described in U.S. Pat. No. 5,510,245, and tetrazolium salts. The chromogen is used in an amount that produces a detectable signal upon its conversion by the hydride abstractor in the presence of reduced cofactor, and can be empirically determined for a given assay system; typical amounts of chromogen range from about 1 µg to about 500 mg for small scale assays.

Exemplary tetrazolium salts that can be used or tested for their applicability as chromogens in a particular embodiment of the invention include: nitroblue tetrazolium chloride (NBT; 2H-(Tetrazolium,-3,3'-(3,3'-dimethoxy(1,1'-biphenyl)-4,4'-diyl)bis(4-nitrophenyl)-5-(phenyl), dichloride); 3-(4,5-Dimethyl-2-thiazolyl)-2,5-diphenyl-2H-tetrazolium bromide (MTT; thiazolyl blue); iodonitrotetrazolium chloride (INT; 2-(4-Iodophenyl)-3-(4-nitrophenyl)-5-phenyl-2H-tetrazolium chloride; iodonitrotetrazolium violet); 3-(4-Iodophenyl)-2-(4-nitrophenyl)-5-phenyl-2H-tetrazolium chloride; neotetrazolium chloride (NTC; 2,2',5, 5'-Tetraphenyl-3,3'-[p-diphenylene] ditetrazolium chloride); tetranitro tetrazolium blue chloride (TNBT; 2,2',5,5'-Tetra(4-nitrophenyl)-3,3'-dimethoxy-4,4'-biphenylene)-2H,2H'-ditetrazolium chloride); tetrazolium Blue chloride (BT; blue tetrazolium chloride; 2,2',5,5'-Tetraphenyl-3,3'-(3,3'-dimethoxy-4,4'-biphenylene)-2H,2H'-ditetrazolium chloride); triphenyltetrazolium chloride (TTC; tetrazolium red; 2,3,5-Triphenyl-2H-tetrazolium chloride); triphenyltetrazolium bromide (TTB; 2,3,5-Triphenyl-2H-tetrazolium bromide); 4-[3-(4-Iodophenyl)-2-(4-nitrophenyl)-2H-5-tetrazolio]-1,3-benzene disulfonate (WST 1); 4-[3-(4-Iodophenyl)-2-(2,4-dinitrophenyl)-2H-5-tetrazolio]-1,3-benzenedisulfonate (WST 3); 2-Benzothiazolyl-3-(4-carboxy-2-methoxyphenyl)-5-[4-(2-sulfoethylcarbamoyl) phenyl]-2H-tetrazolium salt (WST 4); 2,2'-dibenzothiazolyl-5,5'-bis(4-di(2-sulfoethyl)carbamoylphenyl)-3,3'-(3,3'-dimethoxy-4,4'-biphenylene)ditetrazolium, disodium salt (WST-5); Sodium 3,3'-{1-[(Phenylamino)carbonyl]-3,4-tetrazolium}-bis(4-methoxy-6-nitro)benzenesulfonic acid hydrate (XTT); 2-(2'-benzothiazolyl)-5-styryl-3-(4'-phthalhydrazidyl)tetrazolium (BSPT); 2-benzothiazolyl-(2)-3,5-diphenyl tetrazolium (BTDP); 2,3-di(4-nitrophenyl) tetrazolium (DNP); 2,5-diphenyl-3-(4-styrylphenyl) tetrazolium (DPSP); distyryl nitroblue tetrazolium (DS—NBT); 2-phenyl-3-(4-carboxyphenyl)-5-methyl tetrazolium (PCPM); thiocarbamyl nitroblue tetrazolium (TCNBT; 2,2'-Di(p-nitrophenyl)-5,5'-di(p-thiocarbamylphenyl)-3,3'-(3,3'-dimethoxy-4,4'-biphenylene)ditetrazolium chloride); 5-cyano-2,3-di-4-tolyl-tetrazolium chloride (CTC); Nitrotetrazolium Violet (NTV); p-Anisyl Blue Tetrazolium Chloride (pABT); m-Nitro Neotetrazolium Chloride (m-NNT); o-Tolyl Tetrazolium Red (o-TTR); p-Tolyl Tetrazolium Red (pTTR); Piperonyl Tetrazolium Blue (PTB); p-Anisyl-p-Nitro Blue Tetrazolium Chloride (pApNBT); Veratryl Tetrazolium Blue (VTB); and tetrazolium violet (TV; 2,5-Diphenyl-3-(alpha-naphthyl)tetrazolium chloride), all of which are commercially available (e.g., Fluka, Calbiochem, Serva, Sigma-Aldrich, Amersham Biosciences, Connect Marketing GmbH (Buchs, Switzerland)) and/or can be synthesized via published techniques.

Stabilizing agents may be included in the assay or any component thereof to prevent degradation of performance. For example, where a tetrazolium salt is used as the chromogen, an oxidizing agent may be incorporated to inhibit the premature formation of the formazan dye and/or to oxidize interfering substances, thus lowering the background of the assay. Any oxidizing agent that can inhibit formation of the formazan and/or oxidize an interfering substance may be used in an amount effective for such use; exemplary oxidizing agents include the compounds described in U.S. Pat. Nos. 4,743,559 to Koever et al., 4,892,817 to Pawlak, and 5,583,006 to Storhoff et al., for example iodates, permanganates such as potassium permanganate, manganese dioxide, sodium chlorate, 2,5-dimethylhexane-2,5-dihydroperoxide, benzoyl peroxide, t-butylperoxide, sodium iodate, N-ethylmaleimide, t-butylperoxyacetate, nickel acetylacetonate, stannic chloride, rhodium (mi) trichloride hydrate, and t-butylperbenzoate.

Composition for Assaying a Sample for GHB

A composition for assaying a sample for a GHB source is also provided. The composition comprises a first oxidoreductase that can oxidize GHB to succinic semialdehyde, an oxidized cofactor for the first oxidoreductase that is reduced upon oxidation of GHB by the first oxidoreductase, a second oxidoreductase that can oxidize the reduced cofactor produced by the first oxidoreductase, and a chromogen or dye that is detectably converted upon oxidation of the reduced cofactor by the second oxidoreductase. The components of the composition are provided in forms and amounts effective to produce a detectable change in the chromogen or dye upon contacting the composition with a sample comprising GHB. The other optional components of the assay described throughout this application may also independently be included in the composition, including without limitation a buffer, a surfactant, an additional enzyme or enzymes for converting a precursor of GHB to GHB, an additional enzyme for converting ethanol to a compound not yielding a false positive test for GHB, a stabilizing agent, and an oxidizing agent. The composition can be provided on, embedded within, or otherwise associated with a support.

Stabilized Formulation Comprising the First Oxidoreductase

A stabilized formulation comprising the first oxidoreductase is also provided. Such a formulation allows storage of the purified and/or isolated first oxidoreductase while retaining enzyme activity. The formulation comprises an active form of the first oxidoreductase and a stabilizing agent. The stabilizing agent is selected from polyalcohols such as glycerol, azides such as sodium azide, ammonium sulfate, a polyethylene glycol, and a suger (e.g., sucrose) and combinations thereof. The first oxidoreductase can be a succinic semialdehyde reductase, for example a *R. eutropha* SSA reductase or fusion thereof.

Figure 5:
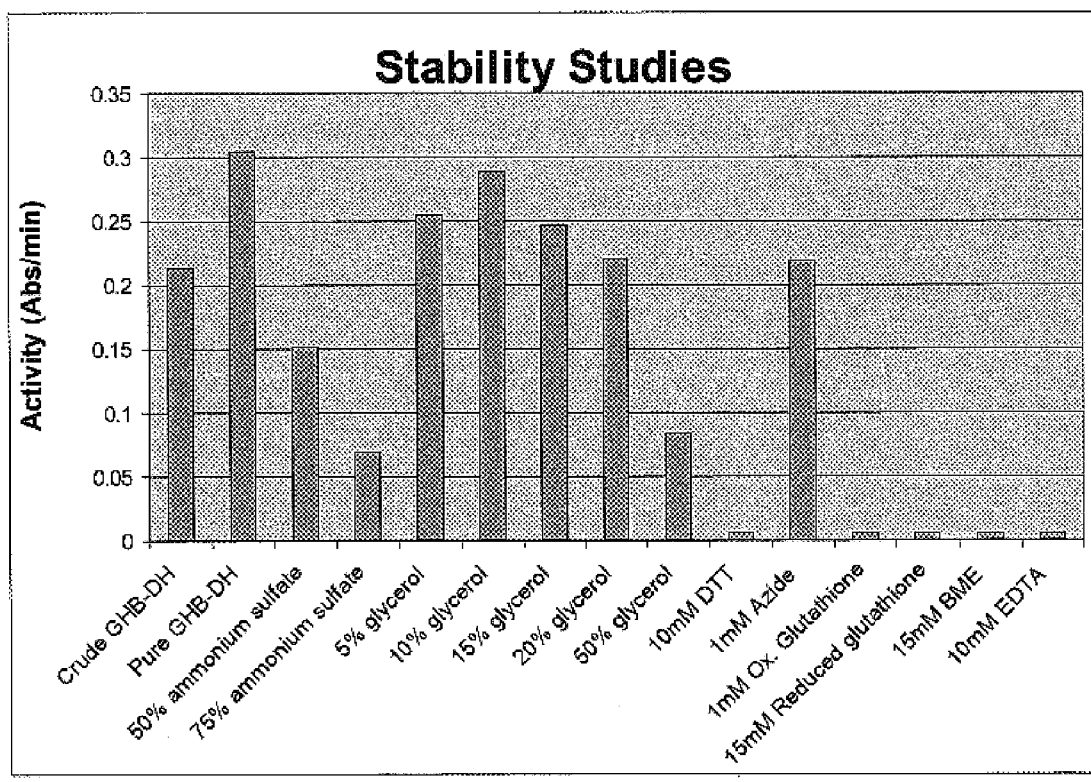
FIG. 5 presents the effects of potential stabilization agents on the enzymatic activity of GHB-DH fusion protein stored for 21 days at 4° C. Activity was determined using the assay of FIG. 4A. Details are given in Example 6.

A number of potential stabilizing agents were tested for their suitability in stabilizing a formulation of a GST fusion protein comprising the *R. eutropha* SSA reductase. Enzymatic activity of the purified fusion protein was studied after storage in different formulations for 21 days at 4° C. The fusion protein retained 82% of its activity after 21 days (FIG. 5; "Pure GHB-DH") and 60% activity after 3.5 months (not shown) at 4° C. in resuspension buffer. A range of concentrations of ammonium sulfate and glycerol were tested. Formulations comprising ammonium sulfate lost 50% or more of the enzyme activity during storage. Formulations comprising from 5–20% glycerol retained high degrees of enzyme activity during storage, with 10% glycerol showing the greatest retention at 21 days (FIG. 5). The fusion protein also retained 80% activity indefinitely when stored at −20° C. or −80° C. in 50% glycerol (data not shown). Formulations comprising 1 mM sodium azide also retained a high degree of enzyme activity during storage at 4° C. Reducing agents including dithiothreitol (DTT), reduced glutathione, and beta-mercaptoethanol drastically diminished enzyme activity, as did oxidized glutathione. Additionally, the chelating agent ethylene diamine tetraacetic acid also drastically diminished enzyme activity. GHB-DH may contain bound iron and copper ions (Wolf, 1995), which chelating agents can sequester and thereby denature and/or inactivate the oxidoreductase.

The Support

The assay can be performed on a support, on the surface thereof and/or within permeable supports. The support is not limited as to material so long as the assay can be performed and the results determined. The support can comprise a wide range of material, either biological, nonbiological, organic, inorganic, or a combination of any of these. The support may be porous and/or absorbent, and may be bibulous or non-bibulous. The support is desirably insoluble in water and other physiological fluids. Exemplary substances from which the support is formed include filter paper, sponge materials, cellulose, wood, woven and nonwoven fabrics, glass fiber, polymeric films, preformed or microporous membranes (e.g., nylon), hydrophilic inorganic powders (e.g., silica gel, alumina, and diatomaceous earth), argillaceous substances, cloth, hydrophilic natural polymeric materials (e.g., cellulose materials, cellulosic beads, etc.), natural and synthetic fibers, fiber-containing papers such as filter paper or chromatographic paper, synthetic or modified naturally-occurring polymers, such as crosslinked gelatin, cellulose acetate, nitrocellulose, polyvinyl chloride, polyacrylamide, cellulose, polyvinyl alcohol, polysulfones, polyesters, polyacrylates, polyurethanes, crosslinked dextran, agarose, and other such crosslinked and non-crosslinked polymers. The support can be of different chemical compositions or a mixture of chemical compositions. The support is most advantageously constructed from bibulous filter paper or nonbibulous polymeric films.

The support may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly) vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonates, or combinations thereof.

Supports can be planar crystalline supports such as silica based supports (e.g. glass, quartz, or the like), or crystalline supports used in, e.g., the semiconductor and microprocessor industries, such as silicon, gallium arsenide and the like.

Silica aerogels can also be used as supports, and can be prepared by methods known in the art. Aerogel supports may be used as free-standing supports or as a surface coating for another support material.

Exemplary forms which the support may take include a sheet, strip, plate, slide, bead, pellet, disk, particle, strand, precipitate, optionally porous gel, tube, sphere, container, capillary, pad, slice, film, chip, multiwell plate or dish, an optical fiber, etc. The support may contain raised or depressed regions on which assay reagents may be conjugated and/or deposited. The surface of the support can be etched using well known techniques to provide for desired surface features, for example trenches, v-grooves, mesa structures, or the like.

Surfaces on the support can be composed of the same material as the support or can be made from a different material, and can be attached to the support by chemical or physical means. Such attached surfaces may be composed of any of a wide variety of materials, for example, polymers, plastics, resins, polysaccharides, silica or silica-based materials, carbon, metals, inorganic glasses, membranes, or any of the above-listed support materials. The surface can be optically transparent and can have surface Si-OH functionalities, such as those found on silica surfaces.

The support and/or its optional surface are chosen to provide appropriate optical characteristics for the assay methods used. The support and/or surface can be transparent to allow the exposure of the support by light applied from multiple directions. The support and/or surface may be provided with reflective "mirror" structures to increase the recovery of light.

The support and/or its surface is generally resistant to, or is treated to resist, the conditions to which it is to be exposed in use, and can be optionally treated to remove any resistant material after exposure to such conditions.

The support and/or its surface can comprise material with low-protein binding characteristics, and/or can be treated to decrease protein binding to decrease undesirable nonspecific background binding by components of the sample. Exemplary materials and techniques to decrease nonspecific protein binding are described by Zyomyx, Inc. in U.S. Pat. No. 6,329,209 and Int'l. Pat. Pubs. Nos. WO 01/72458, WO 01/63241, WO 01/62887, WO 01/51912, WO 00/04390, WO 00/04389, and WO 00/04382.

One or more of the assay reagents can be conjugated to the support; suitable conjugation techniques are known in the art. For example, one or both of the oxidoreductases can be conjugated to the support using an appropriate activator of the support, such as cyanogen bromide (Hitzeman et al., J. Biol. Chem. 255:12073, 1980) or epichlohydrin for cellulose paper or aminopropyl silane for glass. In addition to cyanogen bromide conjugation and silation, other exemplary conjugation chemistries include diazo conjugation (e.g., diazobenzyloxymethyl conjugation (Renart et al., Proc. Natl. Acad. Sci. 76:3116, 1979), diazophenylthio conjugation (Seed et al., Nucleic Acids Res. 10:1799, 1982)), carbodiimide conjugation, glutaraldehyde conjugation, aminobenzyloxymethyl conjugation, 2-aminophenylthioether conjugation, nitrobenzyloxymethyl conjugation, dichlorotriazine conjugation, cyanuric chloride conjugation (Hunger et al., Biochim. Biophys. Acta 653:344, 1981) and the use of heterobifunctional reagents. Activated nylon can also be used. For a review on conjugation chemistries, see Renart and Sandoval, Methods Enzymol. 104:455, 1984. Spacers or linkers can be incorporated in conjugating any of the reagents to the support. Exemplary spacers or linkers include polyethyleneglycols, dicarboxylic acids, polyamines, alkylenes, diamino alkyl or aryl groups, aryl carboxylic acid or gamma-amino alkyl groups, thiol, hydroxyl and mercurated bases. The spacers or linkers are optionally substituted with functional groups, for example hydrophilic groups such as amines, carboxylic acids and alcohols or lower alkoxy group such as methoxy and ethoxy groups. Additionally, the spacers can comprise an activated site for ease of linkage. The active sites can be optionally protected initially by protecting groups. Among a wide variety of protecting groups that are useful are FMOC, BOC, t-butyl esters, t-butyl ethers, and the like. Various exemplary protecting groups are described in, for example, Atherton et al., Solid Phase Peptide Synthesis, IRL Press (1989).

A linker conjugated to the support also might be comprised of a protein or peptide able to form a binding pair with one or both oxidoreductases or one or both derivatized oxidoreductases. Examples of potential protein and peptide spacers are glutathione, antibodies directed against one or both oxidoreductases, and functional fragments of antibodies directed against one or both oxidoreductases. Avidin and streptavidin proteins conjugated to the support also can be used to anchor one or both oxidoreductases derivatized by biotin or biotin-containing homologue. Combinations and variations of such methods also can be devised.

A test support comprising reagents for performing the assay is also provided. The test support comprises a support, a first oxidoreductase that can oxidize GHB to succinic semialdehyde (SSA), an oxidized cofactor that is reduced by the first oxidoreductase to a reduced cofactor upon oxidation of GHB, and a hydride abstractor that can oxidize the reduced cofactor and produce a detectable change. The hydride abstractor may be a second oxidoreductase. A chromogen or dye may be included that is detectably converted by the hydride abstractor upon oxidation of the reduced cofactor. Other components of the assay may also optionally be incorporated with the support as described above with regards to the assay, for example a buffer that provides a suitable pH for the assay to occur. Any or all of the reagents independently may be conjugated to, deposited within, encased by, impregnated in, or otherwise associated with the support in any fashion that allows the assay to be performed. Additional reagents may be provided to the support in solution, in combination with the sample and/or separately.

The support may be in the form of a test strip, for example a strip of fibrous material such as paper, of nitrocellulose, or of a membrane. Any form of test strip known in the art for assaying analytes may be adapted to perform the methods described herein. Exemplary test strips are described in U.S. Pat. No. 5,611,995, U.S. Pat. No. 5,510,245, U.S. Pat. No. 5,912,139, U.S. Pat. No. 6,190,918, U.S. Pat. No. 3,915,639, U.S. Pat. No. 6,153,147, U.S. Pat. No. 4,092,115, and U.S. Pat. No. 3,715,192. The latter two patents describe the use of wicks or capillaries whereby the sample is drawn into the encased support, which is separated from the bulk of the sample. The support may be incorporated into a multilaminate structure as described in U.S. Pat. No. 5,902,731; the sample may pass through certain of the layers to reach the support layer where the assay is to occur. The layers through which the sample passes may be designed or treated to remove and/or alter undesired components of the sample.

The support can be retained within a housing in a manner that allows introduction of the sample to the support but can protect the bulk of the support from undesired manipulation. The housing can provide structural strength for the support, and may serve to separate the components of the method of the invention, for example from the bulk of the sample. The particular shape of the housing is not critical. The housing can provide one or more "window(s)" or aperture(s) that allow viewing of a portion of the support to determine whether a detectable change in the chromogen has occurred. The aperture(s) may be open, or may be covered with a transparent covering. Alternatively, the housing may be made of a transparent material.

One or more positive controls may be included with the test support, and may be located on the test support itself or on a separate support. Where the positive control is located on the test support, it is located so that the reaction product resulting from the positive control can be distinguished from the reaction product produced as a result of GHB present in the sample. The particular arrangement of the positive control is not critical as long as its signal can be distinguished from that of the sample. A variety of arrangements of positive controls are known in the art. For example, a support may comprise a "cross" or "plus" sign wherein one strip of reagents for performing the positive control reaction is localized on the support in a line forming the horizontal part of the plus sign, and a strip of reagents for performing the test reaction on the sample is localized in a vertical line perpendicular to and intersecting the horizontal strip for the positive control reagent(s). Development of only the positive control can thus appear as a "minus" or negative sign in the absence of a GHB source, whereas in the presence of GHB, a "plus" sign appears indicating a positive test from development of both the positive control and the test reaction on the sample. Alternatively, the support may be retained in a housing that has separate apertures for viewing the results from the sample and from the positive control reaction, which may occur on the same or different supports.

Exemplary reagents that may be used to generate positive control signals in the absence of GHB in the sample include the reduced cofactor, and GHB or a GHB precursor. Any of the reagents may be localized on the support, for example through conjugation and/or entrapment, whether in the form of patterns or otherwise. In addition to the cofactor, the first oxidoreductase and the hydride abstractor may also be localized, as can the chromogen and any additional enzymes used, e.g. esterases. One or more of the reagents may be allowed to diffuse through the support upon contact with the liquid sample so long as the reaction in the presence of GHB produces a detectable signal. Some of the tetrazolium compounds produce insoluble products, which may be deposited and thereby localized on the support even in the absence of conjugation of the chromogen or of the hydride abstractor to the support.

Assays can be performed with different chromogens and/ or dyes localized on different regions of the support, or on different supports. The different chromogens and/or dyes produce detectably different color changes, and preferably produce widely separated color changes. At least 2, 3, 4, 5, 6, 7, 8 or more different chromogens and/or dyes can by used. In this way, multiple assays can be performed on the same sample. This arrangement has at least two benefits: it can provide for confirmation of a positive result, especially a weak positive result; and it can permit detection of a positive result from a GHB-containing sample whose inherent color interfered with detection of a positive signal in an assay containing a single chromogen or dye.

Devices can be utilized for performing the methods of the invention in any format which produces a detectable result, including the formats disclosed herein. Devices known in the art for testing liquid samples may be adapted to perform the disclosed GHB assay, including the liquid samplers described in U.S. Pat. No. 3,965,750, U.S. Pat. No. 3,994, 170, U.S. Pat. No. 4,157,664, U.S. Pat. No. 4,625,574, U.S. Pat. No. 5,583,044, and U.S. Pat. No. 5,728,076.

As described above, the assay may be performed with one or more reagents localized on a support, and with one or more reagents allowed to diffuse through the support in a chromatographic fashion. Assays that allow reagents such diffusion have been termed "migration assays," and a number of methods and devices for performing such assays are known in the art and can be adapted to perform the methods disclosed herein. Exemplary migration-type assays and devices that may be adapted include those described by Tom et al. in U.S. Pat. No. 4,366,241, by Zuk in EP-A 0 143 574, by Bernstein in U.S. Pat. No. 4,770,853, by May et al. in WO 88/08534, by Ching et al. in EP-A 0 299 428, by Valkirs et al. in U.S. Pat. No. 4,632,901, and by Korom et al. in EP-A 0 299 359.

A number of so-called "dipstick" devices for assaying analytes are known in the art, wherein a device comprising a support on which an assay is performed is "dipped" into a liquid sample. The act of dipping may initiate performance of the assay without further steps, or additional processing steps may be performed to complete the assay. The assay described herein may be performed on a dipstick device; a dipstick device comprising reagents for performing the methods of the invention is also provided. The particular form of the dipstick device is not critical. Dipstick devices known in the art that may be adapted to perform the methods of the invention include the devices described in EP-A 0 125 118 by Baxter et al., EP-A 0 282 192 by Kali et al., U.S. Pat. No. 4,313,734 by Leuvering, U.S. Pat. No. 4,786,589 by Rounds, and in U.S. Pat. No. 5,656,448.

Additionally, a search of the U.S. Food and Drug Administration ("FDA") web site 510(k) listings for devices named "pregnancy test" reveals approximately 168 such tests. Many of these are in the form of at-home test kits for testing urine samples for the presence of hormones associated with pregnancy, and can be adapted to perform the methods described herein. Examples of such pregnancy tests include Clearblue Easy®, Answer, Answer Quick & Simple® One-step, Be Sure® 1 Step, FIRST RESPONSE® Early Result, dBEST® One Step Rapid Test strip or cassette for hCG, My Secret™ hCG dipstrip, E.P.T.®, E.P.T. Plus®, ClearPlan® and ClearPlan Easy®, Clearview Easy hCG, Fact Plus® One Step, Fact Plus® Select One Step, FIRST RESPONSE® Early Result, Quidel Home, Affirm One-Step Home, Quickstick One Step, Advance®, Predictor Home and FirstDay Early, as well as those described in U.S. Pats. Nos. 5,786,220, 5,770,460, 5,776,961, 6,235,241, 6,187,269 and 5,504,013.

Detection of GHB in Alcoholic Beverages

Detection of GHB in alcoholic beverages by the enzymatic methods disclosed herein is extremely rapid and sensitive. Titration experiments indicated that the method can detect GHB in beverages at concentrations at least as low as 1 mM (FIG. 9), far below typical concentrations used for GHB abuse.

Ethanol is an alternative substrate for the R. eutropha SSA reductase (also known as GHB-DH). It binds about 200-fold less tightly than GHB does (see Example 7). Under conditions in which the amount of diaphorase activity present greatly exceeds GHB-DH activity, the slow rate-limiting step in the coupled assay is the rate of catalysis by GHB-DH. The relatively weak binding of ethanol to GHB-DH then can be the basis for an assay 200-fold more responsive to GHB than to ethanol. When GHB-DH and a high concentration of diaphorase were covalently linked to filter paper, an assay selective for GHB was achieved (see Example 8). However, color development was relatively slow, which suggests that the covalent attachment method used denatured much of the GHB-DH.

Purified commercial diaphorase is expensive, and purified commercial GHB-DH may also be costly. Thus, a dipstick assay for GHB using a lower ratio of diaphorase to GHB-DH activity and less GHB-DH was sought. However, decreasing the ratio of diaphorase to GHB-DH activity was expected to decrease the ability of the assay to discriminate between ethanol and GHB, as the rate-limiting step in color development would shift from the GHB-DH reaction to the diaphorase reaction.

The expected decrease in selectivity for GHB under such conditions was confirmed in a study comparing the intensity of purple color produced by different concentrations of ethanol with the intensity produced by 20 mM GHB in the same concentrations of ethanol (Table 1). Samples containing 20 mM GHB produced intense purple in all cases. Samples containing no GHB but 5% or more ethanol produced definite color, and at 40% and 50% ethanol, the color was as intense as for 20 mM GHB. Samples containing no GHB but 1% or less ethanol produced little or no color. Thus, samples containing 1% or less ethanol (e.g., a physiologic fluid) can be assayed for GHB under these conditions without prior treatment to remove ethanol.

TABLE 1

| Percent Ethanol | Relative Color Intensity on Paper[a] (++++ equal 20 mM GHB containing no ethanol) |
|---|---|
| 1 | ± |
| 5 | ++ |
| 10 | ++ |
| 20 | +++ |
| 40 | ++++ |
| 50 | ++++ |

[a]The conditions of Example 9 were used with 1 min of reaction.

Samples containing 20 mM GHB in ethanol developed more intense color than samples containing only the same concentration of ethanol. However, in a field situation, a person testing an alcoholic beverage for possible adulteration by GHB generally would not be able to compare the result with that from a closely similar alcoholic beverage known to lack GHB. Thus a sample containing 5% or more ethanol and lacking GHB produces sufficient color development to constitute a false positive result in this format. Therefore, to perform assays in this test format when using an SSA reductase from R. eutropha, or an enzyme with similar selectivity, as the first oxidoreductase, samples that might contain 5% or more ethanol such as beverages are preferably treated in a manner that removes ethanol in order to avoid false positives from ethanol.

Any method that can remove ethanol from the sample without removing significant amounts of GHB or otherwise adversely affecting the assay can be used. Preferably, methods are used that are easily portable for use in field tests, although laboratory methods can be used, for example in clinical or forensic settings.

One method to eliminate ethanol is to modify the alcohol so as to render it unusable as a substrate for the first oxidoreductase. This can be accomplished by using an alcohol dehydrogenase, which may be a quinonoid alcohol dehydrogenase, specific or highly selective for ethanol as compared to GHB.

Another method to prevent a false positive test due to ethanol is to evaporate the ethanol from the sample, as GHB and GHB precursors in all of their forms are much less volatile than ethanol is. Any evaporative technique effective for removing ethanol without deleteriously affecting the other components of the assay can be used, including air drying, solvent assisted drying (e.g., using acetone and/or isopropanol), heating techniques, blowing techniques, and combinations thereof. Evaporative techniques involving heating a support after deposition of the sample are presented in Examples 9–11. The other components of the assay can then be added to the evaporated sample.

Any method of heating that does not otherwise prevent the effective performance of the method may be used. The supports can be heated in an oven, for example a conventional oven, a laboratory drying oven, or a microwave oven. Heating filter papers impregnated with sample for 1 minute in a typical microwave at high power was found to evaporate the ethanol and thereby avoid possible ethanol interference. Any powered heating device can in principle be used, including battery-powered heaters, for example of the kind used for handwarmers in winter climates. Potentially the lens of a flashlight can be used. Chemically powered devices may also be used, including chemical heating pads (e.g. Thermo-Pad, Hood Thermo-Pad Canada Ltd., Summerland, BC), and thin-film batteries that can produce power and heat when wet (e.g., Power Paper™, Power Paper, Ltd., New York, N.Y. and Tel Aviv, Israel; powerpaper.com) as described in U.S. Pat. Nos. 5,652,043, 5,811,204 and 5,897,522.

Chromatographic methods can also be used to separate ethanol in the sample from GHB. Additionally, selective membrane techniques can be used to separate ethanol and GHB in the sample.

Figure 8:
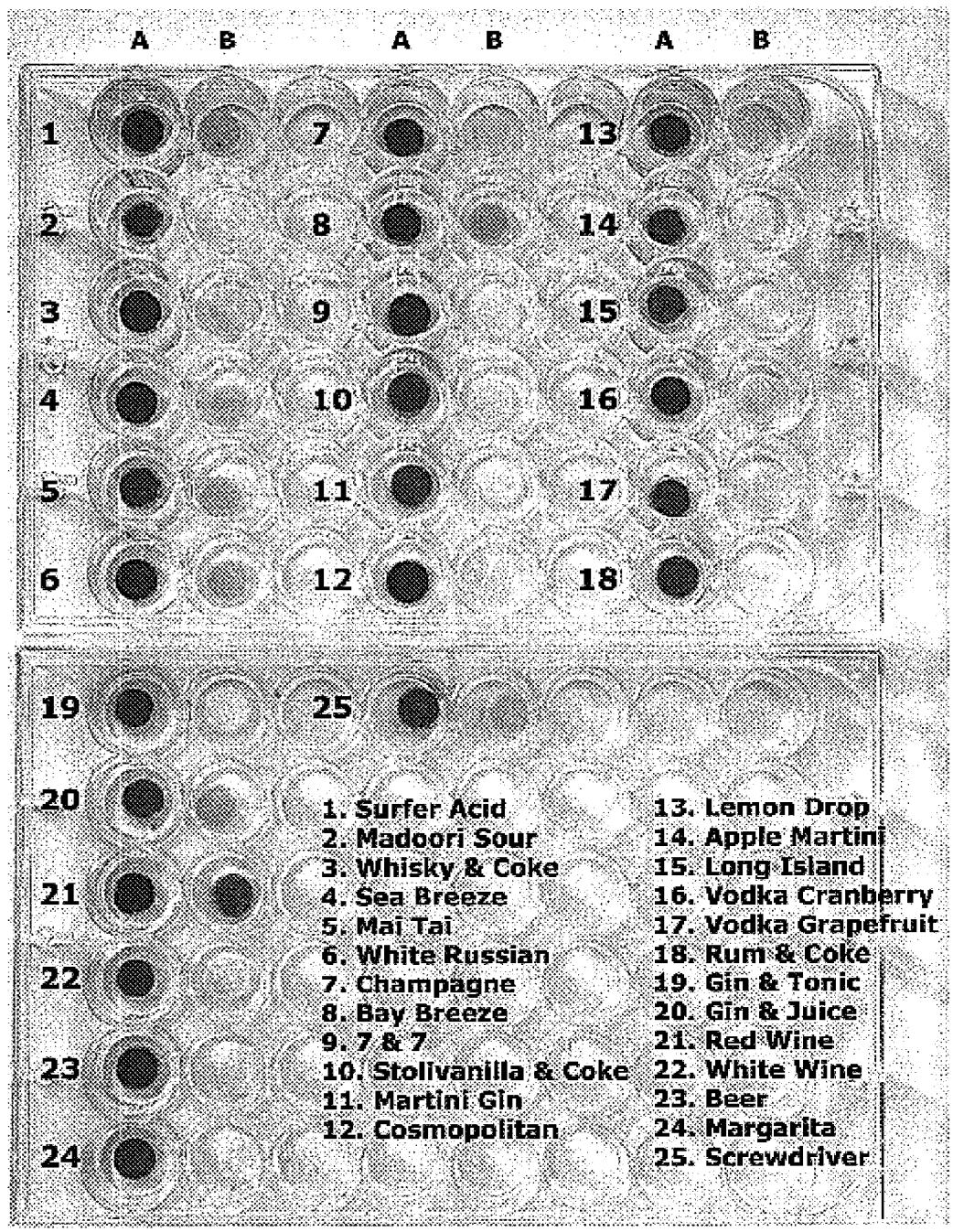
FIG. 8 presents model "dipstick" tests on common alcoholic beverages tainted or not tainted with GHB. A GHB concentration 4-fold less than commonly abused was studied. Beverages are identified in the lower right corner. Ten µl of each sample was applied to a circle of filter paper that then was heated to evaporate the ethanol, which otherwise produces a false positive test under the conditions used here. Ten µl of a solution containing $NAD^+$, the chromogen MTT, pH 8.5 buffer and smaller amounts of GHB-DH fusion protein and diaphorase than used in FIG. 7 was applied to each filter. Color was allowed to develop for 2 minutes. All tainted beverages produced a deep purple color (A columns). Only red wine produced a significantly colored filter in the absence of GHB (B columns). Although the colors of red wine and reduced MTT can be distinguished, a more definite distinction between untainted and tainted red wine could be obtained by use of (1) a chromogen yielding a different color or (2) a smaller amount of sample. Details are given in Example 9.

One other potential source of interference was seen in a test of the assay on a panel of alcoholic beverages of various types, with and without GHB (Example 10 and FIG. 8). Red wine was found to stain the filter paper in the absence of GHB even after heat evaporation (Sample 21B in FIG. 8). The filter color produced by unadulterated red wine was visually distinguishable from the purple produced from the MTT chromogen (FIG. 8). Incorporation of a positive control on the support would therefore allow a positive signal to be distinguished from the background color of unadulterated red wine in a field test, particularly where the test reagent(s) formed a pattern on the support. Other chromogens having colors more distinguishable from the red wine background could also be used, including fluorescent chromogens. Alternatively, because of the sensitivity of the method, smaller amounts of samples containing red wine could be tested, and this procedure would produce a positive signal with lower levels of background. Also, the samples could be diluted prior to application to the support.

Kits

Kits comprising reagents useful for performing the methods of the invention are also provided. In one embodiment, a kit comprises a first oxidoreductase that can oxidize GHB to succinic semialdehyde (SSA), an oxidized cofactor for the first oxidoreductase, and a hydride abstractor that can abstract hydride from the reduced cofactor produced by the first oxidoreductase upon oxidation of GHB. The hydride abstractor is preferably a second oxidoreductase as described above. A chromogen or dye as described above is preferably included in the kit. One or more of the components of the kit may be provided on a support on which the assay is to be performed. The support may be retained within a housing, and may be provided in the form of a device, such as a dipstick device, for performing the assay. The kit may optionally comprise a reagent for converting a precursor of GHB to GHB, for example an oxidoreductase (alcohol dehydrogenase, aldehyde dehydrogenase), esterase, amidase, or combination thereof.

The components of the kit are retained by a case, which can be of any material suitable for retaining the components. Instructions for using the kit to perform a method of the invention are provided with the case, and may be located inside the case or outside the case, and may be printed on the interior or exterior of any surface forming the case that renders the instructions legible.

EXAMPLES

The following examples are set forth so as to provide those of ordinary skill in the art with a complete description of how to make and use the present invention, and are not intended to limit the scope of what is regarded as the invention. Efforts have been made to ensure accuracy with respect to numbers used (e.g., amounts, temperature, etc.) but some experimental error and deviation should be accounted for. Unless otherwise indicated, parts are parts by weight, temperature is degree centigrade and pressure is at or near atmospheric, and all materials are commercially available.

Example 1

Cloning of a coding sequence for a GHB dehydrogenase (GHB-DH) and preparation of a GST fusion protein vector. *Ralstonia eutropha* had previously been shown to express a GHB dehydrogenase (Valentin, 1995). Total genomic DNA was isolated from *R. eutropha* (ATCC, Rockville, Md.) using the Bactozol DNA isolation kit (Molecular Research Center Inc., Cincinnati, Ohio). Synthetic oligonucleotide primers were designed to amplify the GHB-DH gene with BamHI and EcoRI restriction sites added to the 5' and 3' ends of the sense strand of the gene, respectively (Gibco-BRL, Rockville, Md.). Polymerase chain reaction (PCR) amplification of GHB-DH coding sequence and the appended restriction sites then was carried out. The amplified fragment of DNA (1.1 kb) was purified by electrophoresis and trimmed with BamHI and EcoRI restriction endonucleases (New England Biolabs Inc., Beverly, Mass.) to generate sticky ends. The glutathione S-transferase (GST) fusion vector pGEX-2T (Amersham-Pharmacia Biotech Inc., Piscataway, N.J.) was linearized with BamHI and EcoRI restriction enzymes. The purified and trimmed DNA coding for GHB-DH was ligated into the linearized pGEX-2T fusion vector, creating a GST/GHB-DH recombinant vector (pGEX-2T/GHB-DH). Sequence analysis of the recombinant vector using the Sequenase kit (Amersham Life Science Corp., Cleveland, Ohio) confirmed that the GHB-DH coding sequence was in-frame with the GST coding sequence. The recombinant vector was transformed into *E. coli* XL1-Blue cells (Stratagene Corp., San Diego, Calif.) and grown at 37° C. in Luria-Bertani (LB) medium (Difco Corp., Sparks, Md.) containing ampicillin (100 µg/ml) for maintenance and amplification of the vector. The GHB-DH coding sequence also was cloned into other expression vectors that produced the GHB-DH polypeptide tagged on the C-terminus with polyhistidine. These constructs produced little or no GHB-DH activity when expressed.

Example 2

Expression of GHB-DH fusion protein. Recombinant vector was transformed into *E. coli* pLysS cells (Novagene Corp., Madison Wis.) for expression. The transformed cells were grown in 1 L of 2×YTA medium (16 gm Tryptone, 10 gm yeast extract, 5 gm NaCl with 100 µg of ampicillin per ml) to an $OD_{600}$ of 0.8 at 37° C. Expression of soluble fusion protein was induced at 20° C. with 0.1 mM isopropyl β-D-thiogalactoside (IPTG) and allowed to continue for 18–20 hours. Induction at 37° C. resulted in most of the induced protein appearing as an insoluble inclusion body that made it difficult to use the GHB-DH produced. Subsequent steps were carried out at 4° C. Cells were harvested by centrifugation and resuspended in 12.5 ml of 30 mM MOPS adjusted to pH 7.4 with NaOH and also containing 50 mM NaCl (resuspension buffer), 0.15 mM phenylmethylsulfonyl fluoride and 2 µg aprotinin per ml (Sigma Chemical Corp., St. Louis, Mo.). The cell suspension was sonicated on ice and clarified by centrifugation.

Example 3

Figure 3A:
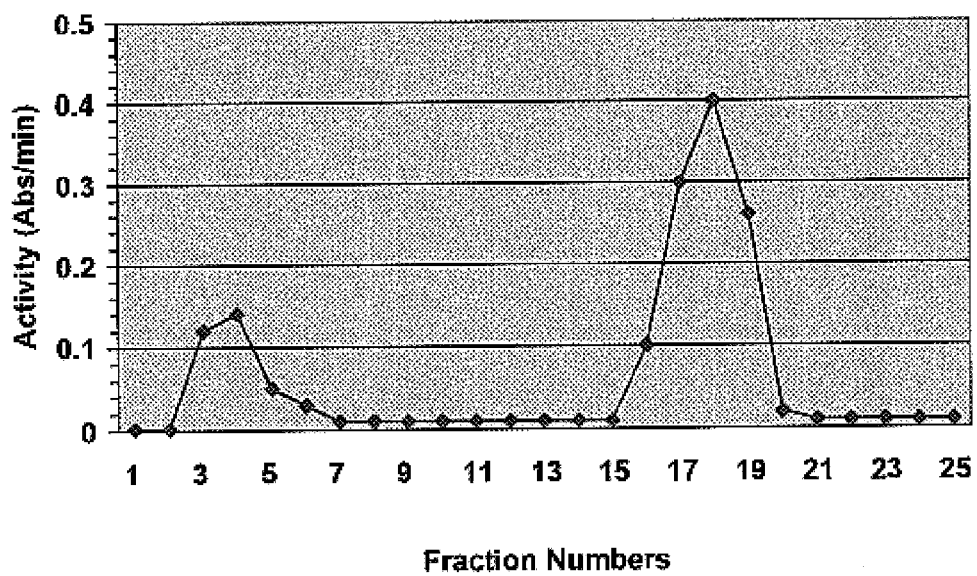
FIG. 3A shows GHB-DH enzymatic activity exhibited by fractions collected during purification of a first oxidoreductase that is a fusion protein comprising *R. eutropha* GHB-DH fused to a glutathione-binding fragment of glutathione S-transferase (GST) on a glutathione (GSH) affinity column. Activity was assayed using the method in FIG. 4A. Fractions 3 and 4 are the breakthrough fractions in which unbound protein from the clarified supernatant appeared. Fraction numbers 17, 18 and 19 were pooled for further experiments. Details are given in Example 3.
Figure 3B:
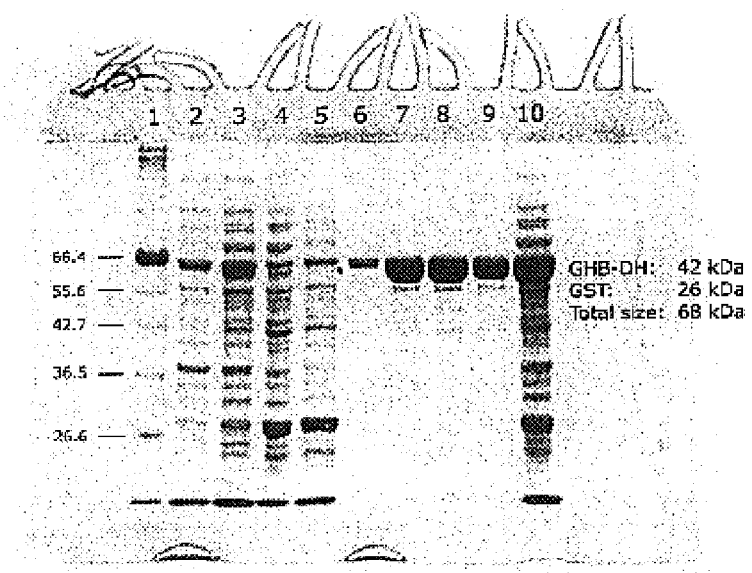
FIG. 3B shows the results of sodium dodecyl sulfate-polyacrylamide gel electrophoresis (SDS-PAGE) of samples collected during purification of GHB-DH fusion protein. Lane 1 contains $M_r$ markers. Lanes 2–5 contain samples from column fractions 3–6 as shown in FIG. 3A. Lanes 6–9 contain samples from column fractions 16–19 as shown in FIG. 3A. Lane 10 contains a sample of the clarified supernatant before loading onto the GSH column. Details are given in Example 3.

Purification of the GHB-DH fusion protein. Affinity resin (4 g) containing covalently bound glutathione (GSH) (Sigma Chemical Corp., St. Louis, Mo.) was swelled in water. The swollen resin was packed into a 50 ml capacity chromatography column and had a capacity of 5 mg/ml. Subsequent steps were carried out at 4° C. The resin was equilibrated by flowing 75 ml of resuspension buffer through the column. Clarified supernatant from the sonicated cells was slowly flowed into the resin after which flow was stopped and fusion protein was allowed to adsorb to the resin for approximately 15 minutes. The loaded affinity resin was washed by flowing 75 ml of resuspension buffer (also containing 1% Tween 20 and 0.45 M additional NaCl) and 75 ml of wash buffer (30 mM MOPS adjusted to pH 7.4 with NaOH) through it. To elute bound GST/GHB-DH fusion protein, 20 ml of 15 mM GSH in wash buffer adjusted to pH 7.0 was flowed into the resin, after which the flow was stopped for 1 hour. The resin was washed with 30 ml more GSH. Fractions (10 ml) were collected throughout, and each was assayed for GHB-DH activity (FIG. 3A) using the method described in Example 4 and polypeptide content (FIG. 3B) determined by SDS-PAGE. Three fractions (17–19) containing most of the enzymatic activity in a fairly pure state were pooled. Protein in the pool was precipitated by the addition of ammonium sulfate to 75% saturation. Precipitated protein was pelleted by centrifugation, and the supernatant was discarded. The pellet was dissolved in 10 ml of resuspension buffer and placed in dialysis tubing of $10^3$ $M_r$ cutoff. The sample was dialyzed in 2 L of resuspension buffer that was replaced four times over a period of 24 hours. The final protein concentration was determined by the Bradford method (Bio-Rad Corp., Hercules, Calif.) with bovine serum albumin as standard. The yield of GHB-DH fusion protein was 213 mg, just below the theoretical capacity of 250 mg for the column (note that fraction 16, which contained protein, was not collected). The true amount of protein produced from the 1-liter culture may have exceeded the capacity of the column.

Example 4

Figure 4A:
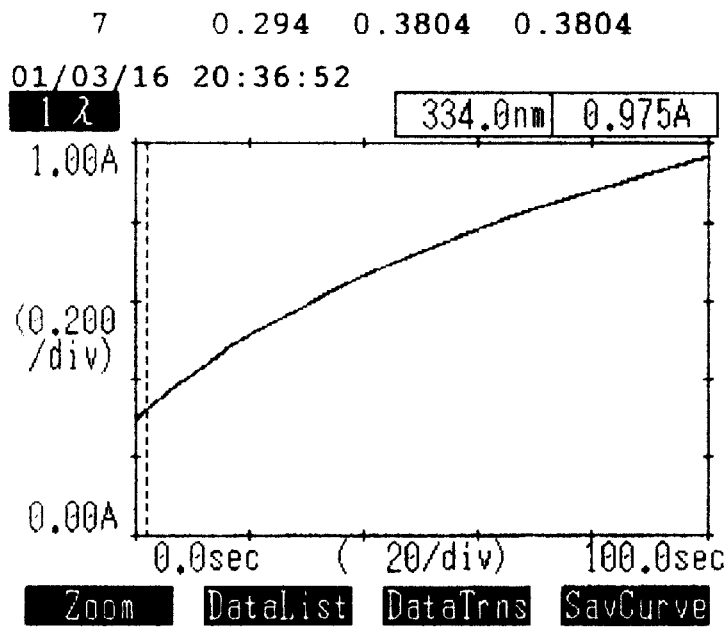
FIG. 4A shows reduction of $NAD^+$ by purified GHB-DH fusion protein and GHB in pH 8.5 buffer. Formation of NADH was monitored at 334 nm. Details are given in Example 4.

Enzymatic assay for GHB based on formation of NADH. GHB-DH activity was assayed at 23° C. in 1 ml of buffer (97 mM 2-amino-2-methyl-1,3-propanediol (AMPD) adjusted to pH 8.5 with HCl) containing 14 μg purified fusion protein and 1 mM NAD$^+$ in a cuvette of 1 cm path length at 23° C. (Valentin, 1995). Reaction was initiated by the addition of GHB to 20 mM, and formation of NADH was monitored by the increase in absorbance at 334 nm (FIG. 4A). The reaction reached apparent (but not true) completion after a few minutes. This was due to approach to equilibrium, as the reverse direction reaction is more favored than the direction being assayed (Kaufman, 1993).

Example 5

Figure 4B:
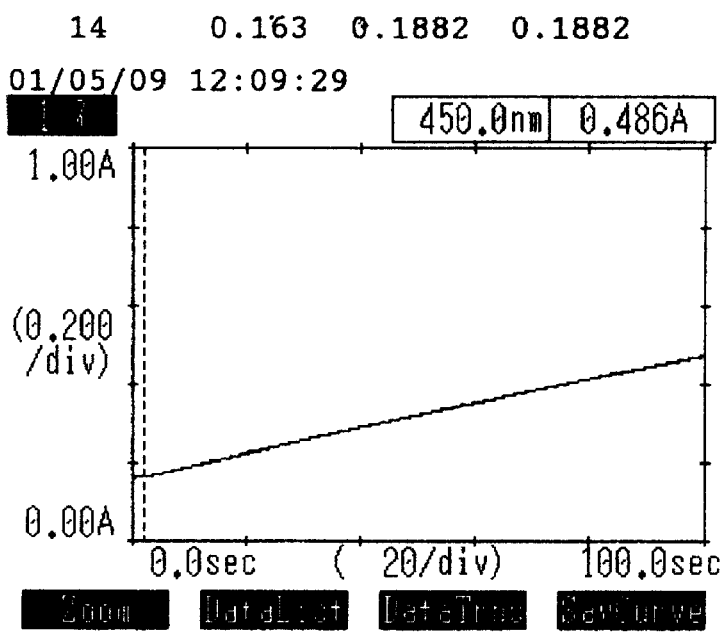
FIG. 4B presents reduction of the chromogen XTT by purified GHB-DH fusion protein, GHB, $NAD^+$ and diaphorase in pH 8.5 buffer. Formation of reduced XTT, which is soluble, was monitored at 450 nm. Details are given in Example 5.

Enzymatic assay for GHB based on formation of a colored product. Diaphorase from *Bacillus stearothermophilus* (Unitika Corp., Japan) was chosen as second oxidoreductase for a coupled enzyme assay, as it is resistant to heat denaturation and should store well. Coupling two oxidoreductase reactions makes the overall reaction yielding SSA and a detectably changed chromogen or dye more favorable than the uncoupled reaction yielding only NADH and SSA. The assay conditions were similar to those in Example 4, except that 5 μg of GHB-DH fusion protein was used, 80 μM of the chromogen sodium 3,3'-{1-[(Phenylamino)carbonyl]-3,4-tetrazolium}-bis(4-methoxy-6-nitro)benzenesulfonic acid hydrate (XTT, Sigma Chemical Corp., St. Louis, Mo.) was included, and different concentrations of diaphorase were tested to determine the amount of second oxidoreductase required for maximal rate of color development. The reaction was monitored at 450 nm in a 1 cm path length cuvette at 23° C. Diaphorase at 0.7 μg was sufficient to give maximal rate of color development. The rate was nearly constant over the first several minutes of reaction (FIG. 4B).

Example 6

Stability of fusion protein. The GHB-DH enzymatic activity of *R. eutropha* GHB-DH fusion protein was studied after storage for 21 days at 4° C. under various conditions (FIG. 5). Fourteen μg of protein was assayed using the method described in Example 4. Test enzyme solutions included the crude lysate, purified fusion protein at 7 mg/ml in 50 mM NaCl and 30 mM MOPS adjusted to pH 7.4 with NaOH, and purified fusion protein at 7 mg/ml in the same buffer also containing potential stabilizing agents. Purified fusion protein stored in the absence of potential stabilizing agents retained 82% of its activity ("Pure GHB-DH") and 60% activity after 3.5 months (not shown). Purified fusion protein retained 80% activity indefinitely when stored at −20° C. or −80° C. in 50% glycerol (data not shown), but this concentration of glycerol was deleterious at 4° C. The disulfide reducing agents dithiothreitol (DTT) and 2-mercaptoethanol (BME) nearly completely inactivated enzyme activity. Both oxidized and reduced GSH also nearly totally inactivated enzyme activity. These latter results demonstrate that it is critical to remove glutathione quickly after eluting GST-fusion protein from the affinity column. Ammonium sulfate also is somewhat deleterious and should be removed quickly after its use to precipitate purified GHB-DH. EDTA nearly totally inactivated enzyme activity, presumably by chelation of metal ions. Azide had a slight deleterious effect. The crude extract ("Crude GHB-DH") retained 54% of its original activity.

Example 7

Kinetic analyses. The equation $v=V_{max}*S/(K_m+S)$ was fit by least-squares regression to initial velocity data obtained using the coupled assay in Example 5, different concentrations of GHB, and 5 μg of fusion protein (Segal, 1997, FIG. 6A). The $K_m$ value was 2.19±0.13 mM and $V_{max}$ value was 0.049±0.001 Absorbance/min/μg fusion protein.

Because a major target application of the invention is testing alcoholic beverages for the presence of GHB, the stability of soluble *R. eutropha* GHB-DH fusion protein in different concentrations of ethanol was studied. The enzyme was stable for long time periods in 5% ethanol, but at higher concentrations of ethanol it denatured in a few minutes in a time-dependent manner. During the study, it was observed that ethanol is an alternative substrate for the *R. eutropha* GHB-DH enzyme. Thus, initial velocity saturation kinetics were studied with ethanol as substrate.

Figure 6:
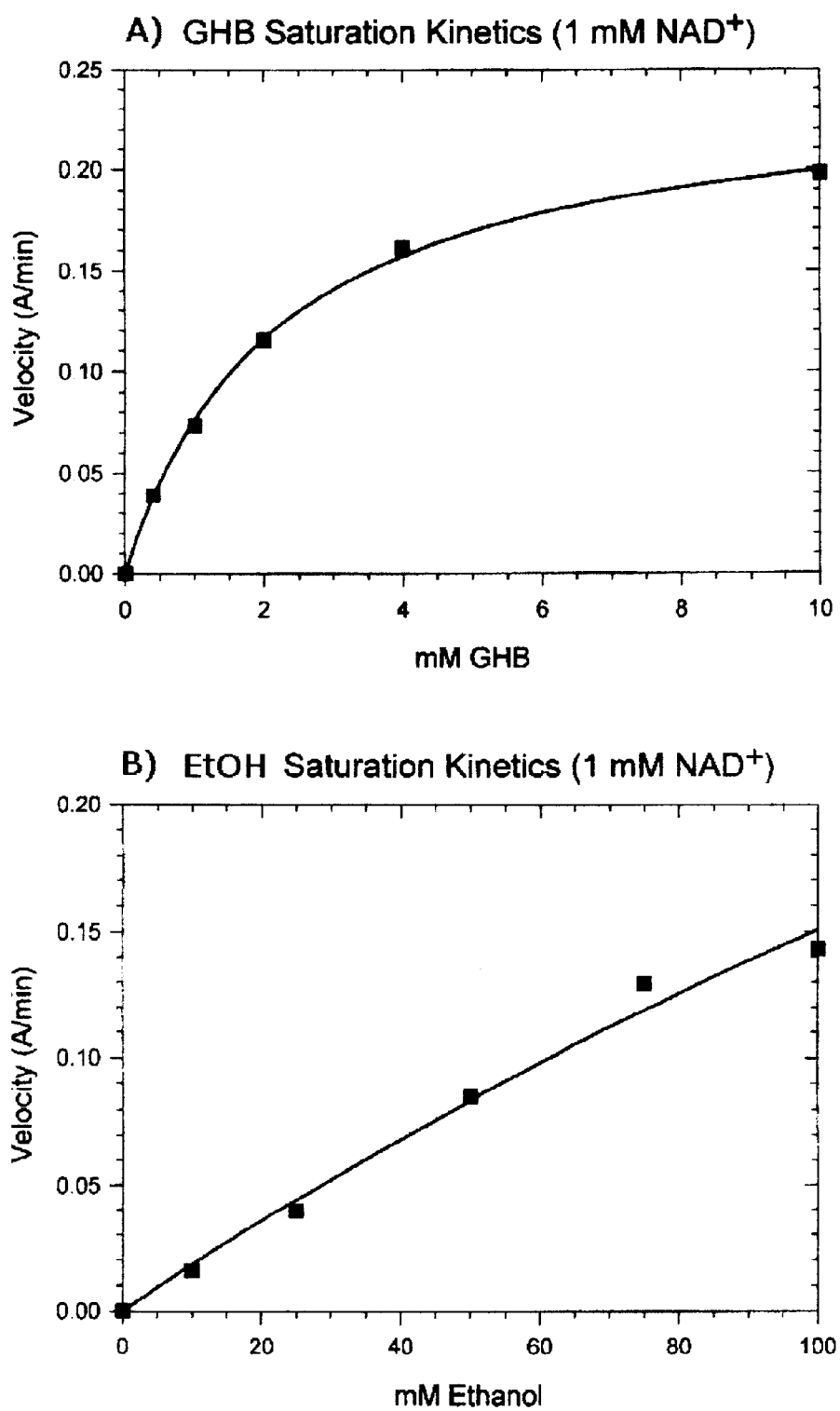
FIG. 6 presents GHB and ethanol saturation kinetics for purified GHB-DH fusion protein. Assay conditions were similar to those used in FIG. 4B except for variable concentrations of substrate. (A) Initial velocities for the indicated concentrations of GHB. The $K_m$ is 2.19±0.13 mM and $V_{max}$ is 0.049±0.001 A/min/µg. (B) Initial velocities for the indicated concentrations of ethanol. If the $V_{max}$ is assumed to be 0.049 A/min/µg (the same as for GHB), the $K_m$ is 413±14 mM. Details are given in Example 7.

Preliminary investigation revealed that ethanol binds to the enzyme too weakly to saturate it at concentrations that do not rapidly denature the enzyme. In order to obtain accurate initial velocity measurements at substantially subsaturating concentrations of ethanol, the amount of GHB-DH fusion protein in the assay was increased to 25 μg. In order to do constrained regression analysis of the limited data available, $V_{max}$ for oxidation of ethanol was assumed to be the same as for GHB. This assumption was based on the high probability that the slow step in steady-state reactions of ethanol and GHB is the same, namely dissociation of NADH. The regression indicated that ethanol has approximately 200 times weaker affinity for the GHB-DH fusion protein than GHB has, with a $K_m$ value of 413±14 mM for an assumed $V_{max}$ of 0.049 A/min/µg (FIG. 6B).

Example 8

Dipstick assay using a solid support. The quantitative assays reported in Example 7 were done in solution, using a spectrophotometer. A semi-quantitative dipstick-type assay suitable for use by minimally trained individuals in a field situation was sought.

Figure 7:
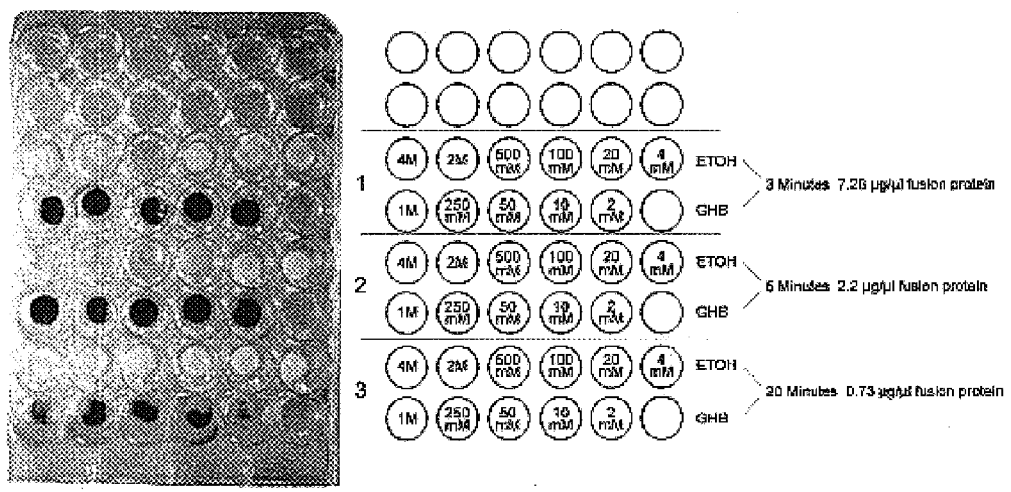
FIG. 7 presents model "dipstick" tests performed on samples containing GHB or ethanol. Filter-paper circles were covalently conjugated to three concentrations of purified GHB-DH fusion protein and a high concentration of diaphorase, after which they were soaked in a solution of $NAD^+$, the chromogen MTT and pH 8.5 buffer and air dried. Circles were incubated in the concentrations of GHB or ethanol indicated by the template on the right for the stated times. Reduced MTT is insoluble and purple, although these results were photographed in black and white. Under these conditions, the test is highly selective for GHB. Two mM of GHB produced a deep purple, and all concentrations of ethanol produced little or no color. Details are given in Example 8.

Twelve Whatman 3 MM CHR paper-filter circles of 6 mm diameter were activated with cyanogen bromide and conjugated overnight at 4° C. in 250 µl of a solution containing 0.1 M $NaHCO_3$ buffer (pH 8.6), 2.8 µg of diaphorase per µl and 0.73, 2.2 or 7.28 µg of GHB-DH fusion protein per µl. The intermediate concentration of fusion protein (2.2 µg/∞l) and this concentration of diaphorase (2.8 µg/∞l) decreased the ratio of fusion protein to diaphorase ten-fold relative to that used in the assay shown in FIG. 6A. This was done in order to increase the likelihood that (1) the rate-limiting step in the coupled reactions would be the GHB-DH step and (2) the assay on paper would exhibit the 200-fold preference for GHB relative to ethanol that was identified in Example 7. Also, because the efficiency of conjugation to the paper support could differ for the two oxidoreductases, ratios of GHB-DH fusion protein to diaphorase 3-fold greater than and 3-fold less than the intermediate ratio were tested. Conjugated filters were washed in 0.1 M $NaHCO_3$ buffer at pH 8.6 containing 6 ml ethanolamine per liter for 30 minutes at 23° C. in order to quench excess activated sites on the paper. The filters then were washed in assay buffer (97 mM 2-amino-2-methyl-1,3-propanediol (AMPD) adjusted to pH 8.5 with HCl) and stored wet at 4° C. Filters were removed from storage and washed in assay buffer containing 2 mM $NAD^+$ and 0.08 mM of the chromogen 3-[4,5-dimethylthiazol-2-yl]-2,5-diphenyl-tetrazolium bromide (MTT). MTT was used instead of XTT because its reduced form is insoluble and deposited on the paper. Filters loaded with $NAD^+$ and chromogen were air dried and tested with various concentrations of GHB and ethanol (FIG. 7). The filters were placed in separate 1 ml solutions containing the indicated concentrations of GHB or ethanol in assay buffer and allowed to react at 23° C. The results were photographed in black and white after the indicated reaction times had elapsed. All filters exposed to GHB rapidly turned intensely purple. Sample series #1 yielded the best overall results. At 3 minutes, these samples had developed little color in ethanol and intensely purple color in all concentrations of GHB tested. Sample series #2 and #3 gave even less color with ethanol, but they turned purple in GHB more slowly than sample series #1 did. GHB concentrations as low as 2 mM were readily detected. Thus, these conditions produced a dipstick test (1) selective for GHB and (2) not subject to a false positive due to ethanol.

Example 9

Economical dipstick assay for GHB in alcoholic beverages. The assays described in Example 8 used relatively large amounts of GHB-DH fusion protein and diaphorase and utilized conjugation of the oxidoreductases to the filter-paper support. These requirements would increase the expense of preparing a dipstick. Because a dipstick likely would be constructed to prevent dissolution of a cofactor such as $NAD^+$ and a chromogen or dye from the dipstick into the sample being tested, immobilization of the oxidoreductases on the dipstick might not be necessary. A test for GHB in alcoholic beverages that required smaller amounts of GHB-DH fusion protein and diaphorase and no conjugation of the oxidoreductases to the support accordingly was sought. The results in Example 7 demonstrated that ethanol is an alternative substrate for the R. eutropha GHB-DH in soluble assays, and the results presented in Table 1 demonstrated that concentrations of ethanol commonly present in alcoholic beverages could generate a false positive for the presence of GHB under certain circumstances. Evaporation of the alcoholic beverages before testing for GHB was therefore chosen as one way to avoid false positives from ethanol, as GHB does not readily evaporate (FIG. 8).

A wide variety of common alcoholic beverages was tested untainted and tainted by GHB. Twenty-five different alcoholic beverages were provided (Michelle Edwards, Radisson Hotel, Santa Barbara, Calif.), as indicated by the key in FIG. 8. A portion of each beverage was taken and made 20 mM in GHB. This concentration is several-fold below the 70–80 mM GHB considered to be typical in a tainted drink. Ten µl of each beverage sample (±GHB) was applied to separate un-activated circles of Whatman 3 MM CHR filter paper. The filters were heated 15 minutes at 80° C. to evaporate ethanol, after which they were allowed to cool to 23° C. Ten µl of a solution containing 670 mM AMPD (pH 8.5 with HCl), 33 mM $NAD^+$, 1.7 µg of the chromogen MTT per µl, 2.3 µg of the GHB-DH fusion protein per µl, and 0.012 µg of diaphorase per µl then was applied to each filter. The concentration of the pH buffer was increased in order to neutralize the large amount of acid found in many alcoholic beverages. The concentration of $NAD^+$ was increased to make the first oxidoreductase reaction step more favorable. The filter immediately started to develop purple color when GHB was present in the alcoholic beverage, and within 1 minute the reaction was 90% complete. Color was allowed to develop for 2 minutes, after which the reaction was quenched with 10% acetic acid. Acetic acid stops the reaction without destroying deposited color so that the results can be viewed and photography can be performed at leisure. All filters developed an intense purple color when GHB was present in the beverage. Sample 21, red wine, developed a deep reddish color in the absence of GHB. Although the colors of red wine and reduced MTT can be distinguished, a better solution could be obtained by use of a chromogen yielding a color more different from that of red wine or by using a smaller amount of sample. Many other chromogens are commercially available. Thus, prior evaporation of an alcoholic beverage on a dipstick can be used to allow detection of GHB using soluble R. eutropha GHB-DH in a wide range of alcoholic beverages without false positives (FIG. 8).

Example 10

Figure 9:
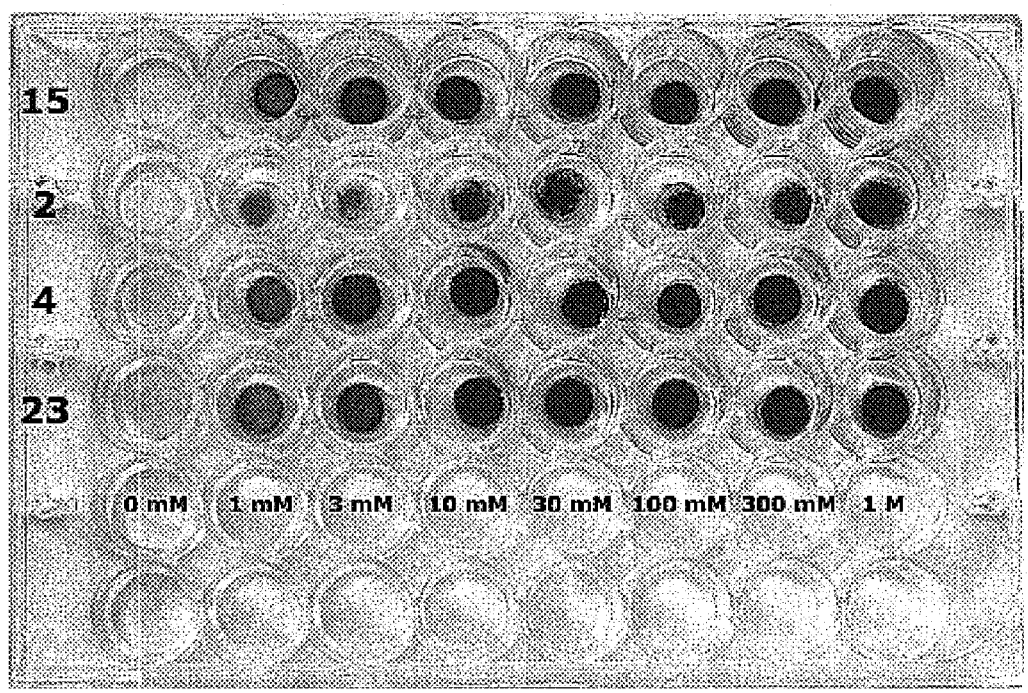
FIG. 9 presents GHB titrations in alcoholic beverages preferred by young women. The method of FIG. 8 was used, and the key in FIG. 8 identifies the beverages. As little as 1 mM of GHB produced clearly visible purple indicating a positive test. Details are given in Example 10.

Titration of GHB detection in alcoholic beverages. Sensitivity for detection of GHB was studied using the assay described in Example 9 on some alcoholic beverages preferred by young women (beverage numbering is given in FIG. 8). The following concentrations of GHB were tested: 0 mM, 1 mM, 3 mM, 10 mM, 30 mM, 100 mM, 300 mM and 1 M. The reaction was allowed to proceed at 23° C. for 2 minutes before quenching with 10 µl of 10% acetic acid (FIG. 9). All filters developed an intense purple color when GHB was present in the beverage, even for the lowest concentration of GHB tested (1 mM). Again, untainted drinks produced no significant purple color. Sample 2, Madoori Sour, produced a blotchy purple deposit when GHB was present. The blotchiness was a characteristic of the drink, but it did not interfere with the ability of the assay to discriminate between positive and negative results. Blotchiness might be prevented by use of surfactant in the assay.

Example 11

Detection of GHB in urine. Sensitivity for detection of GHB in human urine was studied. Sample 1 was 100% urine. Samples 2–6 were prepared with 100 mM GHB. Samples 7–10 were prepared with 2.0 M GHB. The urine concentrations of samples 2–10 were 99.9%, 99.7%, 99.0%, 97.0%, 90.0%, 98.5%, 95.0%, 85.0%, and 50.0%, respectively. Table 2 gives the concentrations of GHB in the samples.

TABLE 2

| # | Conc. (mM) |
|---|---|
| 1 | 0.0 |
| 2 | 0.1 |
| 3 | 0.3 |
| 4 | 1.0 |
| 5 | 3.0 |
| 6 | 10 |
| 7 | 30 |
| 8 | 100 |
| 9 | 300 |
| 10 | 1000 |

Figure 10:
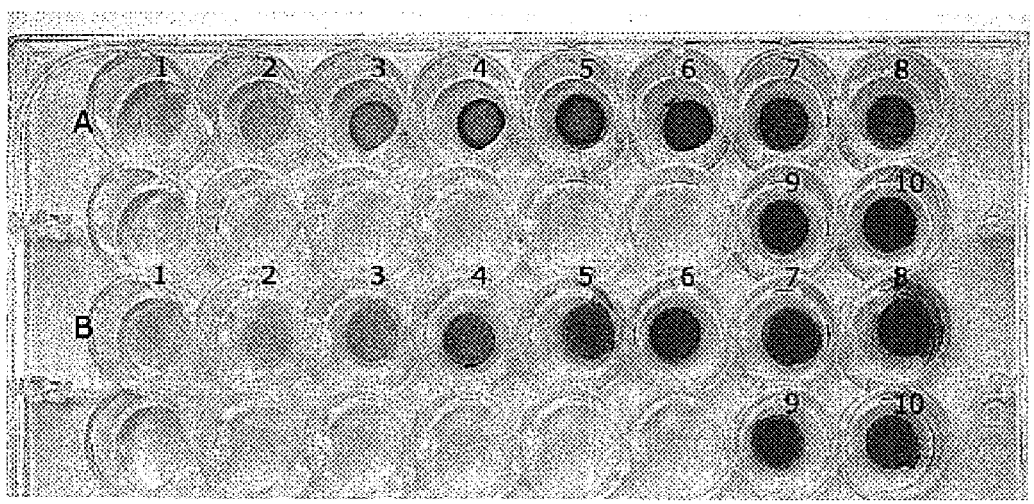
FIG. 10 presents GHB titrations in human urine. The method of FIG. 8 was used, except that the B series of samples was not evaporated prior to the test. Samples 1–10 contained 0 mM, 0.1 mM, 0.3 mM, 1 mM, 3 mM, 10 mM, 30 mM, 100 mM, 300 mM, and 1000 mM GHB, respectively. Untainted urine produced no significant color, and as little as 0.1 mM GHB in urine produced a light purple color, whether or not the sample had been dried. Details are given in Example 11.

Ten $\mu$l of each sample was applied to separate un-activated circles of Whatman 3 MM CHR filter paper. Assay (A) filters were dried at 80° for 10 minutes while assay (B) filters were used immediately without drying. Ten $\mu$l of a solution containing 670 mM AMPD (pH 8.5 with HCl), 33 mM NAD$^+$, 1.7 $\mu$g of the chromogen MTT per $\mu$l, 2.3 $\mu$g of the GHB-DH fusion protein per $\mu$l, and 0.012 $\mu$g of diaphorase per $\mu$l was then added to each filter. The reaction was allowed to proceed for 5 minutes at 23° C. before quenching with 10% acetic acid (FIG. 10). Untainted urine produced no significant color. The lowest concentration of GHB tested (0.1 mM) produced slight but definite purple, while the next higher concentration of GHB (0.3 mM) produced substantial purple. Evaporation of urine had no significant effect on test results.

REFERENCES

Andriamampandry C., Siffert J. C., Schmitt M., Garnier J. M., Staub A., Muller C., Gobaille S., Mark J. & Maitre M. (1998) Cloning of a rat brain succinic semialdehyde reductase involved in the synthesis of the neuromodulator γ-hydroxybutyrate, Biochem J. 334, 43–50.

Cho W. S., Song M. S., Kim G. Y., Kang W. D., Choi E. Y. & Choi S. Y. (1993) Kinetics and mechanism of an NADPH-dependent succinic semialdehyde reductase from bovine brain. Eur. J. Biochem 211, 757–762.

Cho S. W., Hong J. W., Lee S. J. & Choi S. Y. (1996) Inactivation of an NADPH-dependent succinic semialdehyde reductase by o-phthalaldehyde. FEBS Letters 382, 179–182.

Choi E. Y., Sang Y. P., Sang H. J., Song M. S., Cho S. W. & Choi S. Y. (1995) Production and characterization of monoclonal antibodies to bovine brain succinic semialdehyde reductase. J. Neurochem 64, 371–377.

Cromlish J A, Flynn T G. (1985). Identification of pig brain aldehyde reductases with the high-Km aldehyde reductase, the low-Km aldehyde reductase and aldose reductase, carbonyl reductase, and succinic semialdehyde reductase. J Neurochem 44, 1485–1493.

Ellis E M, Hayes J D. (1995) Substrate specificity of an aflatoxin-metabolizing aldehyde reductase. Biochem J 312, 535–541.

Galloway, G. P., Osborne, S. L. F., Seymour, R., Contini, S. E., Smith, D. E. (2000) Abuse and therapeutic potential of gamma-hydroxybutyric acid. Alcohol 20, 263–269.

Henne A., Daniel R., Schmitz R. A. & Gottschalk G. (1999) Construction of environmental DNA libraries in *Escherichia coli* and screening for the presence of genes conferring utilization of 4-hydroxybutyrate. Appl. Environ. Microbiol. 65, 3901–3907.

Hong J. W., Cho S. W., Yoo J. S., Yoo B. K., Lee K. S. & Choi S. Y. (1997) Modulation of the catalytic activity of brain succinic semialdehyde reductase by reaction with pyridoxal 5'-phosphate. Eur. J. Biochem. 247, 274–279.

Jendrossek D., Krüger N. & Steinbüchel A. (1990) Characterization of alcohol dehydrogenase genes of derepressible wild-type *Alcaligenes eutropus* H16 and constitutive mutants. J. Bacteriol. 172, 4844–4851.

Kaufman E. E. & Nelson T. (1981) Kinetics of coupled γ-hydroxybutyrate oxidation and D-glucuronate reduction by an NADP$^+$-dependent oxidoreductase. J. Biol. Chem. 256, 6890–6894.

Kaufman E. E., Relkin N. & Nelson T. (1983) Regulation and properties of an NADP$^+$ oxidoreductase which functions as a γ-hydroxybutyrate dehydrogenase. J. Neurochem. 40, 1639–1646.

Kaufman E. E. & Nelson T. (1991) An overview of γ-hydroxybutyrate catabolism: The role of the cytosolic NADP$^+$-dependent oxidoreductase EC 1.1.1.19 and of a mitochondrial hydroxyacid-oxoacid transhydrogenase in the initial, rate-limiting step in this pathway. Neurochem. Res. 16, 965–974.

Nelson T. & Kaufman E. E. (1994) Developmental time courses in the brain and kidney of two enzymes that oxidize γ-hydroxybutyrate. Dev. Neurosci. 16, 352–358.

Kemmel V., Taleb O., Perard A., Andriamampandry C., Siffert J. C., Mark J. & Maitre M. (1998) Neurochemical and electrophysiological evidence for the existence of a functional γ-hydroxybutyrate system in NCB-20 neurons. Neurosci. 86, 989–1000.

Kopetzki E., Schumacher G. & Buckel P. (1989) Control of formation of active soluble or inactive insoluble baker's yeast α-glucosidase PI in *Escherichia coli* by induction and growth conditions. Mol Gen Genet 216, 149–155.

Kuhn M., Jendrossek D., Fründ C., Steinbüchel A. & Schlegel H. G. (1988) Cloning of the *Alcaligenes eutrophus* alcohol dehydrogenase gene. J. Biobacteriol. 170, 685–692.

Leonard, S. A. (1999) Gamma-hydroxybutyrate effects and regulation. OLR Research Report #99-R-0825.

Nelson T. & Kaufman E. E. (1994) Developmental time courses in the brain and kidney of two enzymes that oxidize gamma-hydroxybutyrate. Dev. Neurosci. 16, 352–358.

Rodriques M. F. A., Valentin H. E., Berger P. A., Tran M., Asrar J., Gruys K. J. & Steinbüchel A. (2000) Polyhydroxyalkanoate accumulation in Burkholderia sp.: a molecular approach to elucidate the genes involved in the formation of two homopolymers consisting of short-chain-length 3-hydroxyalkanoic acids. Appl. Microbiol. Biotechnol. 53, 453–460.

Segal I. H. (1975) Enzyme Kinetics, J. Wiley & Sons, New York, N.Y.

Schaller M., Schaffhauser M., Sans N. & Wermuth B. (1999) Cloning and expression of succinic semialdehyde reductase from human brain. Eur. J. Biochem. 265. 1056–1060.

Söhling B. & Gottschalk G. (1993) Purification and characterization of a coenzyme-A-dependent succinate-semialdehyde dehydrogenase from *Clostridium kluyveri*. Eur. J. Biochem. 212, 121–127.

Söhling B. & Gottschalk G. (1996) Molecular analysis of the anaerobic succinate degradation pathway in *Clostridium kluyveri*. J. Bacteriol. 178, 871–880.

Valentin H. E., Zwingmann G., Schönebaum A. & Steinbüchel A. (1995) Metabolic pathway for biosynthesis of poly(3-hydroxybutyrate-co-4-hydroxybutyrate) from 4-hydroxybutyrate by *Alcaligenes eutrophus*. Eur. J. Biochem. 227, 43–60.

Valentin H. E. & Dennis D. (1997) Production of poly(3-hydroxybutyrate-co-4-hydroxybutyrate) in recombinant *Escherichia coli* grown on glucose. J. Biotech. 58, 33–38.

Valentin H. E., Reiser S. & Gruys K. J. (2000) Poly(3-hydroxybutyrate-co-4-hydroxybutyrate) formation from γ-aminobutyrate and glutamate. Biotechnol. Bioengin. 67, 291–299.

Wolff R. A. & Kenealy W. R. (1995) Purification and characterization of the oxygen-sensitive 4-hydroxybutanoate dehydrogenase from *Clostridium kluyveri*. Prot. Express. Purif. 6, 206–212.

Yoshie N., Goto Y., Sakurai M., Inoue Y. & Chûjô R. (1992) Biosynthesis and n.m.r. studies of deuterated poly(3-hydroxybutyrate) produced by *Alcaligenes eutrophus* H16. Int. J. Biol. Macromol. 14, 81–86.

Although the invention has been described in some detail with reference to the preferred embodiments, those of skill in the art will realize, in light of the teachings herein, that certain changes and modifications can be made without departing from the spirit and scope of the invention. Accordingly, the invention is limited only by the claims.

What is claimed is:

1. A screening method for detecting gamma-hydroxybutyric acid (GHB), comprising:
providing a sample which is suspected of comprising a source of gamma-hydroxybutyric acid (GHB);
providing a first oxidoreductase comprising an enzymatically active polypeptide that can oxidize GHB to succinic semialdehyde (SSA), said polypeptide selected from the group consisting of (a) a GHB dehydrogenase, (b) an SSA reductase, (c) a glucuronate reductase, and (d) an aflatoxin aldehyde reductase;
providing an oxidized cofactor that can be reduced by said first oxidoreductase in oxidizing GHB to SSA;
a first contacting step wherein the sample is contacted with the first oxidoreductase and the oxidized cofactor under conditions in which the first oxidoreductase can oxidize GHB and reduce the oxidized cofactor to a reduced cofactor to produce a sample suspected of comprising the reduced cofactor;
providing a second oxidoreductase that can oxidize the reduced cofactor;
providing a chromogen or dye that is detectably converted upon oxidation of the reduced cofactor by the second oxidoreductase;
a second contacting step wherein the sample suspected of comprising the reduced cofactor is contacted with the second oxidoreductase and the chromogen or dye under conditions in which the second oxidoreductase can oxidize the reduced cofactor and detectably convert the chromogen or dye; and
determining whether the chromogen or dye has been detectably converted which indicates the presence or absence of GHB in the sample.

2. The method of claim 1, wherein the sample comprises ethanol.

3. The method of claim 1, wherein the sample is selected from the group consisting of a comestible, an anabolic supplement, a dietary supplement, a nutritional supplement, an oil, an extract, an elixir, a pharmaceutical preparation, a natural product preparation, a nutraceutical, blood, urine, saliva, plasma, and serum.

4. The method of claim 3, wherein the sample is a comestible selected from the group consisting of a food and a beverage.

5. The method of claim 4, wherein the comestible is a beverage.

6. The method of claim 5, wherein the beverage is water.

7. The method of claim 3, wherein the sample is saliva.

8. The method of claim 3, wherein the sample is urine.

9. The method of claim 3, wherein the sample is blood.

10. The method of claim 3, wherein the sample is plasma.

11. The method of claim 3, wherein the sample is serum.

12. The method of claim 1, wherein the sample is also contacted with an enzyme that converts a precursor or pro-form of GHB to physiologically active GHB under conditions effective for such conversion.

13. The method of claim 12, wherein the enzyme is selected from the group consisting of an esterase, an amidase, an alcohol dehydrogenase, an aldehyde dehydrogenase, and combinations thereof.

14. The method of claim 1, wherein the first oxidoreductase is a glucuronate reductase.

15. The method of claim 1, wherein the first oxidoreductase is a GHB dehydrogenase.

16. The method of claim 1, wherein the first oxidoreductase is an SSA reductase.

17. The method of claim 16, wherein the SSA reductase is *Ralstonia eutropha* SSA reductase.

18. The method of claim 1, wherein the first oxidoreductase is an aflatoxin aldehyde reductase.

19. The method of claim 1, wherein the oxidized cofactor is selected from a nicotinamide cofactor and a flavin cofactor.

20. The method of claim 19, wherein the oxidized cofactor is a nicotinamide cofactor.

21. The method of claim 20, wherein the nicotinamide cofactor is selected from the group consisting of $NAD^+$ and $NADP^+$.

22. The method of claim 21, wherein the nicotinamide cofactor is $NAD^+$.

23. The method of claim 21, wherein the nicotinamide cofactor is $NADP^+$.

24. The method of claim 1, wherein the second oxidoreductase is selected from the group consisting of a diaphorase, a cytochrome b-5 reductase, and an NAD(P)H:menadione oxidoreductase.

25. The method of claim 1, wherein the second oxidoreductase is a cytochrome b-5 reductase.

26. The method of claim 1, wherein the second oxidoreductase is an NAD(P)H:menadione oxidoreductase.

27. The method of claim 26, wherein the second oxidoreductase is a diaphorase.

28. The method of claim 27, wherein the diaphorase is a *Bacillus stearothermophilus* diaphorase.

29. The method of claim 1, wherein a chromogen is provided that is detectably converted to a colored product that can be detected visually by a human.

30. The method of claim 1, wherein a chromogen is provided, said chromogen selected from the group consisting of: nitroblue tetrazolium chloride BT; 2H-(Tetrazolium,-3,3'-(3,3'-dimethoxy(1,1'-biphenyl)-4,4'-diyl)bis(4-nitrophenyl)-5-(phenyl), dichloride); 3-(4,5-Dimethyl-2-thiazolyl)-2,5-diphenyl-2H-tetrazolium bromide (MTT; thiazolyl blue); iodonitrotetrazolium chloride (INT; 2-(4-Iodophenyl)-3-(4-nitrophenyl)-5-phenyl-2H-tetrazolium chloride; iodonitrotetrazolium violet); 3-(4-Iodophenyl)-2-(4-nitrophenyl)-5-phenyl-2H-tetrazolium chloride; neotetrazolium chloride (NTC; 2,2',5,5'-Tetraphenyl-3,3'-[p-diphenylene] ditetrazolium chloride); tetranitro tetrazolium blue chloride (TNBT; 2,2',5,5'-Tetra(4-nitrophenyl)-3,3'-dimethoxy-4,4'-biphenylene)-2H,2H'-ditetrazolium chloride); tetrazolium Blue chloride (BT; blue tetrazolium chloride; 2,2',5,5'-Tetraphenyl-3,3'-(3,3'-dimethoxy-4,4'-biphenylene)-2H,2H'-ditetrazolium chloride); triphenyltetrazolium chloride (TTC; tetrazolium red; 2,3,5-Triphenyl-2H-tetrazolium chloride); triphenyltetrazolium bromide (TTB; 2,3,5-Triphenyl-2H-tetrazolium bromide); 4-[3-(4-

Iodophenyl)-2-(4-nitrophenyl)-2H-5-tetrazolio]-1,3-benzene disulfonate (WST 1); 4-[3-(4-Iodophenyl)-2-(2,4-dinitrophenyl)-2H-5-tetrazolio]-1,3-benzenedisulfonate (WST 3); 2-Benzothiazolyl-3-(4-carboxy-2-methoxyphenyl)-5-[4-(2-sulfoethylcarbamoyl)phenyl]-2H-tetrazolium salt (WST 4); 2,2'-dibenzothiazolyl-5,5'-bis(4-di(2-sulfoethyl)carbamoylphenyl)-3,3'-(3,3'-dimethoxy-4,4'-biphenylene)ditetrazolium, disodium salt (WST-5); Sodium 3,3'-{1-[(Phenylamino)carbonyl]-3,4-tetrazolium}-bis(4-methoxy-6-nitro)benzenesulfonic acid hydrate (XTT); 2-(2'-benzothiazolyl)-5-styryl-3-(4'-phthalhydrazidyl) tetrazolium (BSPT); 2-benzothiazolyl-(2)-3,5-diphenyl tetrazolium (BTDP); 2,3-di(4-nitrophenyl)tetrazolium (DNP); 2,5-diphenyl-3-(4-styrylphenyl) tetrazolium (DPSP); distyryl nitroblue tetrazolium (DS-NBT); 2-phenyl-3-(4-carboxyphenyl)-5-methyl tetrazolium (PCPM); thiocarbamyl nitroblue tetrazolium (TCNBT; 2,2'-Di(p-nitrophenyl)-5,5'-di(p-thiocarbamylphenyl)-3,3'-(3,3'-dimethoxy-4,4'-biphenylene)ditetrazolium chloride); 5-cyano-2,3-di-4-tolyl-tetrazolium chloride (CTC); Nitrotetrazolium Violet (NTV); p-Anisyl Blue Tetrazolium Chloride (pABT); m-Nitro Neotetrazolium Chloride (m-NNT); o-Tolyl Tetrazolium Red (o-TTR); p-Tolyl Tetrazolium Red (pTTR); Piperonyl Tetrazolium Blue (PTB); p-Anisyl-p-Nitro Blue Tetrazolium Chloride (pApNBT); Veratryl Tetrazolium Blue (VTB); and tetrazolium violet (TV; 2,5-Diphenyl-3-(alpha-naphthyl)tetrazolium chloride).

31. The method of claim 30, wherein the chromogen is MTT.

32. The method of claim 30, wherein the chromogen is XTT.

33. The method of claim 1, wherein the sample is assayed to detect the presence of the source of GHB in the sample.

34. The method of claim 1, wherein the sample is assayed to quantitate the source of GHB in the sample.

35. The method of claim 1, wherein the first and second contacting steps occur concomitantly.

36. The method of claim 1, wherein the method is performed on a support.

37. The method of claim 36, wherein the support is selected from the group consisting of a filter, a strip, a microsphere, a chip, a slide, a multiwell plate, a membrane, and an optical fiber.

38. The method of claim 37, wherein the support is a strip.

39. The method of claim 38, wherein the support is a filter.

40. The method of claim 39, wherein the support is a membrane.

41. The method of claim 1, wherein the sample is treated to remove ethanol prior to or simultaneously with the first contacting step.

42. The method of claim 41, wherein the sample is treated by heating to evaporate ethanol.

43. A composition for assaying a sample for gamma-hydroxybutyric acid (GHB) comprising the following components:
  a first oxidoreductase comprising an enzymatically active polypeptide that can oxidize GHB to succinic semialdehyde (SSA), said polypeptide selected from the group consisting of (a) a GHB dehydrogenase, (b) an SSA reductase, (c) a glucuronate reductase, and (d) an aflatoxin aldehyde reductase;
  an oxidized cofactor for the first oxidoreductase that is reduced upon oxidation of GHB by the first oxidoreductase;
  a second oxidoreductase that can oxidize the reduced cofactor produced by the first oxidoreductase; and
  a chromogen or dye that is detectably converted upon oxidation of the reduced cofactor by the second oxidoreductase,
  wherein the components are present in the composition in forms and amounts effective to produce a detectable change in the chromogen or dye upon contacting the composition with a sample comprising GHB.

44. A fusion protein comprising a catalytically active *Ralstonia eutropha* succinic semialdehyde reductase and a heterologous peptide.

45. The fusion protein of claim 44, wherein the fusion protein is purified and/or isolated.

46. A polynucleotide comprising an open reading frame encoding the fusion protein of claim 44.

47. The polynucleotide of claim 46, further comprising transcriptional and translational control signals operatively associated with said open reading frame.

48. A vector comprising the polynucleotide of claim 46.

49. The vector of claim 48, wherein the polynucleotide further comprises transcriptional and translational control signals operatively associated with said open reading frame.

50. A recombinant host cell comprising a polynucleotide encoding the fusion protein of claim 44.

51. The recombinant host cell of claim 50, wherein the polynucleotide further comprises transcriptional and translational control signals operatively associated with said open reading frame.

52. A stabilized formulation comprising a stabilizing agent and a catalytically active protein selected from a *Ralstonia eutropha* SSA reductase, a fusion protein comprising *Ralstonia eutropha* SSA reductase, a *Ralstonia eutropha* SSA reductase deletion mutant, and a fusion protein comprising a *Ralstonia eutropha* SSA reductase deletion mutant.

53. The stabilized formulation of claim 52, wherein the stabilizing agent is selected from the group consisting of a polyalcohol, an azide, a polyethyleneglycol, a sugar and combinations thereof.

54. The stabilized formulation of claim 53, wherein the stabilizing agent is a polyalcohol.

55. The stabilized formulation of claim 54, wherein the stabilizing agent is glycerol.

56. The stabilized formulation of claim 53, wherein the stabilizing agent is an azide.

57. A test support comprising:
  a support;
  a first oxidoreductase operably associated with the support, wherein the first oxidoreductase can oxidize gamma-hydroxybutyrate (GHB) to succinic semialdehyde (SSA);
  an oxidized cofactor for the first oxidoreductase operably associated with the support, wherein the oxidized cofactor is reduced to a reduced cofactor by the first oxidoreductase upon oxidation of GHB to SSA;
  and a hydride abstractor operably associated with the support that can oxidize the reduced cofactor and produce a detectable color change on the support.

58. The test support of claim 57, wherein the hydride abstractor is a second oxidoreductase.

59. The test support of claim 57, further comprising a chromogen operably associated with the support that is reduced by the hydride abstractor to produce the detectable color change.

60. The test support of claim 57, further comprising a buffer.

61. The test support of claim 57, wherein the support is selected from the group consisting of a filter, a strip, a microsphere, a chip, a slide, a multiwell plate, a membrane, and an optical fiber.

62. The test support of claim 61, wherein the support is a strip.

63. The test support of claim 61, wherein the support is a filter.

64. The test support of claim 61, wherein the support is a membrane.

65. A dipstick device comprising a housing and the test support of claim 57 received within the housing.

66. A kit for assaying a sample for a gamma-hydroxybutyric acid (GHB) source comprising:
   a first oxidoreductase that can oxidize GHB to succinic semialdehyde;
   an oxidized cofactor for the first oxidoreductase that is reduced upon oxidation of GHB by the first oxidoreductase;
   a second oxidoreductase that can oxidize the reduced cofactor produced by the first oxidoreductase;
   a chromogen or dye that is detectably converted upon oxidation of the reduced cofactor by the second oxidoreductase;
   a case for retaining the first oxidoreductase, the oxidized cofactor, the first oxidoreductase and the chromogen or dye; and
   instructions provided with said case that describe how to use the components of the kit to assay a sample for a source of gamma-hydroxybutyric acid.

67. The kit of claim 66, further comprising a support retained within the housing, wherein at least one of the first oxidoreductase, the oxidized cofactor, the second oxidoreductase and the chromogen are operably associated with the support.

68. The method of claim 1, wherein the first oxidoreductase is recombinantly produced.

69. The method of claim 1, wherein the first oxidoreductase is a fusion protein.

70. The stabilized formulation of claim 53, wherein the stabilizing agent is a sugar.

71. The stabilized formulation of claim 70, wherein the sugar is sucrose.

72. A screening method for detecting GHB in a sample, comprising:
   providing a sample which is suspected of comprising gamma-hydroxybutyric acid (GHB);
   providing a first oxidoreductase comprising an enzymatically active polypeptide from *Ralstonia eutropha* GHB dehydrogenase;
   providing an oxidized nicotinamide cofactor that can be reduced by said first oxidoreductase in oxidizing GHB to SSA;
   providing a diaphorase that can oxidize the reduced nicotinamide cofactor;
   providing a tetrazolium salt;
   contacting the sample with the first oxidoreductase, the oxidized nicotinamide cofactor, the diaphorase and the tetrazolium salt under conditions in which the first oxidoreductase can oxidize GHB and reduce the oxidized nicotinamide cofactor to a reduced nicotinamide cofactor and the diaphorase can oxidize the reduced nicotinamide cofactor and detectably convert the tetrazolium salt to a colored product; and
   determining whether the tetrazolium salt has been converted to the colored product which indicates the presence or absence of GHB in the sample.

73. A composition for assaying a sample for gamma-hydroxybutyric acid (GHB) comprising the following components:
   a first oxidoreductase comprising an enzymatically active polypeptide from *Ralstonia eutropha* GHB dehydrogenase;
   an oxidized nicotinamide cofactor for the first oxidoreductase that is reduced upon oxidation of GHB by the first oxidoreductase;
   a diaphorase that can oxidize the reduced nicotinamide cofactor produced by the first oxidoreductase; and
   a tetrazolium salt that is detectably converted upon oxidation of the reduced cofactor by the second oxidoreductase,
   wherein the components are present in the composition in forms and amounts effective to convert the tetrazolium salt to a colored product upon contacting the composition with a sample comprising GHB.

\* \* \* \* \*

SEQUENCE LISTING

<160> NUMBER OF SEQ ID NOS: 2

<210> SEQ ID NO 1
<211> LENGTH: 382
<212> TYPE: PRT
<213> ORGANISM: Ralstonia eutropha
<220> FEATURE:
<223> OTHER INFORMATION: 4-hydroxybutyrate dehydrogenase

<400> SEQUENCE: 1

```
Met Ala Phe Ile Tyr Tyr Leu Thr His Ile His Leu Asp Phe Gly Ala
 1               5                  10                  15

Val Ser Leu Leu Lys Ser Glu Cys Glu Arg Ile Gly Ile Arg Arg Pro
             20                  25                  30

Leu Leu Val Thr Asp Lys Gly Val Val Ala Ala Gly Val Ala Gln Arg
         35                  40                  45

Ala Ile Asp Ala Met Gln Gly Leu Gln Val Ala Val Phe Asp Glu Thr
     50                  55                  60

Pro Ser Asn Pro Thr Glu Ala Met Val Arg Lys Ala Ala Ala Gln Tyr
 65                  70                  75                  80

Arg Glu Ala Gly Cys Asp Gly Leu Val Ala Val Gly Gly Gly Ser Ser
                 85                  90                  95

Ile Asp Leu Ala Lys Gly Ile Ala Ile Leu Ala Thr His Glu Gly Glu
            100                 105                 110

Leu Thr Thr Tyr Ala Thr Ile Glu Gly Gly Ser Ala Arg Ile Thr Asp
        115                 120                 125

Lys Ala Ala Pro Leu Ile Ala Val Pro Thr Thr Ser Gly Thr Gly Ser
    130                 135                 140

Glu Val Ala Arg Gly Ala Ile Ile Ile Leu Asp Asp Gly Arg Lys Leu
145                 150                 155                 160

Gly Phe His Ser Trp His Leu Leu Pro Lys Ser Ala Val Cys Asp Pro
                165                 170                 175

Glu Leu Thr Leu Gly Leu Pro Ala Gly Leu Thr Ala Ala Thr Gly Met
            180                 185                 190

Asp Ala Ile Ala His Cys Ile Glu Thr Phe Leu Ala Pro Ala Phe Asn
        195                 200                 205

Pro Pro Ala Asp Gly Ile Ala Leu Asp Gly Leu Glu Arg Gly Trp Gly
    210                 215                 220
```

His Ile Glu Arg Ala Thr Arg Asp Gly Gln Asp Arg Asp Ala Arg Leu
225                 230                 235                 240

Asn Met Met Ser Ala Ser Met Gln Gly Ala Met Ala Phe Gln Lys Gly
                245                 250                 255

Leu Gly Cys Val His Ser Leu Ser His Pro Leu Gly Gly Leu Lys Ile
            260                 265                 270

Asp Gly Arg Thr Gly Leu His His Gly Thr Leu Asn Ala Val Val Met
        275                 280                 285

Pro Ala Val Leu Arg Phe Asn Ala Asp Ala Pro Thr Val Val Arg Asp
    290                 295                 300

Asp Arg Tyr Ala Arg Leu Arg Arg Ala Met His Leu Pro Asp Gly Ala
305                 310                 315                 320

Asp Ile Ala Gln Ala Val His Asp Met Thr Val Arg Leu Gly Leu Pro
                325                 330                 335

Thr Gly Leu Arg Gln Met Gly Val Thr Glu Asp Met Phe Asp Lys Val
            340                 345                 350

Ile Ala Gly Ala Leu Val Asp His Cys His Lys Thr Asn Pro Lys Glu
        355                 360                 365

Ala Ser Ala Ala Asp Tyr Arg Arg Met Leu Glu Gln Ser Met
    370                 375                 380

<210> SEQ ID NO 2
<211> LENGTH: 1149
<212> TYPE: DNA
<213> ORGANISM: Ralstonia eutropha
<220> FEATURE:
<223> OTHER INFORMATION: 4-hydroxybutyrate dehydrogenase

<400> SEQUENCE: 2

```
atggcgttta tctactatct gacccacatc cacctggatt tcggcgcggt aagcctgctc    60
aagtccgaat gcgagcgcat cggcatccgc cgccgttgc tggtgaccga caagggcgtg   120
gtcgccgcgg gagtggcgca gcgtgccatc gatgcaatgc agggcctgca ggttgcggta   180
ttcgatgaaa ccccgtcgaa cccgaccgag gccatggtgc gcaaggccgc cgcacaatac   240
cgcgaggccg gctgcgacgg gctggtggca gtgggcggcg gctcgtcgat cgacctcgcc   300
aagggcatcg ccatcctggc cacgcatgag gcgagctga ccacctatgc caccatcgaa   360
ggcggcagcg ccaggatcac cgacaaggcg gcgccgctga tcgcggtgcc caccacctcg   420
ggcaccggca gcgaggtggc gcgcggcgcc atcatcatcc tggacgacgg ccgcaagctg   480
ggcttccatt cctggcattt gctgcccaag tccgccgtct gcgacccgga actgacgctg   540
gggctgccgg ccgggctgac cgcggccacc ggcatggatg cgatcgcgca ctgcatcgag   600
accttcctgg ccccgccctt caaccccgcc gcggacggca ttgcgctgga cgggctggag   660
cgcggctggg gccatatcga acgcgccacc cgcgacggtc aggaccgcga cgcacgcctg   720
aacatgatga gcgcgtcgat gcagggcgca atggcgttcc agaagggcct ggcctgcgtg   780
cattcgctgt cgcacccgct gggcgggctg aagatcgacg gccgcaccgg cctgcaccac   840
ggcacgctca acgcggtggt gatgccggcg gtgctgcgct tcaacgccga tgcgcccacg   900
gtggtgcgcg acgaccgcta cgcacgcctg cgccgcgcca tgcacctgcc cgacggcgcc   960
gatatcgcgc aggccgtgca cgacatgacc gtgcgcctgg gcctgcccac gggctgcgt  1020 cagatgggtg tcaccgagga catgttcgac aaggtgattg ccggtgcgct ggtcgaccat  1080
```

```
tgccacaaga ccaacccgaa agaagccagc gccgcggatt atcggcgtat gcttgagcag    1140
tccatgtag                                                             1149
```